US011236302B2

(12) United States Patent
Kirkeby et al.

(10) Patent No.: US 11,236,302 B2
(45) Date of Patent: Feb. 1, 2022

(54) METHODS AND COMPOSITIONS FOR PRODUCING STEM CELL DERIVED DOPAMINERGIC CELLS FOR USE IN TREATMENT OF NEURODEGENERATIVE DISEASES

(71) Applicant: BIOLAMINA AB, Sundbyberg (SE)

(72) Inventors: Agnete Kirkeby, Copenhagen (DK); Malin Pernilla Parmar, Lund (SE)

(73) Assignee: BIOLAMINA AB, Sundbyberg (SE)

( * ) Notice: Subject to any disclaimer, the term of this patent is extended or adjusted under 35 U.S.C. 154(b) by 146 days.

(21) Appl. No.: 16/414,848

(22) Filed: May 17, 2019

(65) Prior Publication Data
US 2019/0300853 A1 Oct. 3, 2019

Related U.S. Application Data

(62) Division of application No. 15/093,927, filed on Apr. 8, 2016, now Pat. No. 10,344,259.

(60) Provisional application No. 62/300,000, filed on Feb. 25, 2016, provisional application No. 62/182,051, filed on Jun. 19, 2015, provisional application No. 62/145,467, filed on Apr. 9, 2015.

(51) Int. Cl.
C12N 5/0797 (2010.01)
C12N 5/0793 (2010.01)
A61K 35/545 (2015.01)
A61K 35/30 (2015.01)

(52) U.S. Cl.
CPC ........... C12N 5/0623 (2013.01); A61K 35/30 (2013.01); A61K 35/545 (2013.01); C12N 5/0619 (2013.01); C12N 2500/38 (2013.01); C12N 2501/119 (2013.01); C12N 2501/13 (2013.01); C12N 2501/15 (2013.01); C12N 2501/41 (2013.01); C12N 2501/727 (2013.01); C12N 2501/999 (2013.01); C12N 2506/02 (2013.01); C12N 2533/52 (2013.01)

(58) Field of Classification Search
None
See application file for complete search history.

(56) References Cited

U.S. PATENT DOCUMENTS

| 2004/0214324 | A1 | 10/2004 | Isacson et al. | |
|---|---|---|---|---|
| 2007/0212777 | A1* | 9/2007 | Reubinoff | C12N 5/0606 435/325 |
| 2012/0009676 | A1* | 1/2012 | Mack | C12N 15/85 435/372 |
| 2015/0265652 | A1* | 9/2015 | George | C12Q 1/6876 424/93.21 |
| 2016/0215260 | A1* | 7/2016 | Takahashi | C12N 5/0619 |

FOREIGN PATENT DOCUMENTS

| WO | 2008120218 A2 | 10/2008 |
|---|---|---|
| WO | 2011156331 A2 | 12/2011 |
| WO | 2015034012 A1 | 3/2015 |

OTHER PUBLICATIONS

Benton et al. "Multiple uses of basement membrane-like matrix (BME/Matrigel) in vitro and in vivo with cancer cells." International Journal of Cancer 128.8 (2011): 1751-1757. (Year: 2011).*
Yan et al. "Directed differentiation of dopaminergic neuronal subtypes from human embryonic stem cells." Stem Cells 23(6): 781-790, 2005 (Year: 2005).*
Invitrogen Life Technologies, Cat. No. 23017-015, "Natural Mouse Laminin." May 2010, pp. 1-2.
BioLamina LAMSCREEN, 2014(online), retrieved on Feb. 26, 2020, <URL:https://web.archive.org/web/20140912182046/http://www.biolamina.com/lamscreen>.
Daisuke et al., "Isolation of Human Induced Pluripotent Stem Cell-Derived Dopaminergic Progenitors by Cell Sorting for Successful Transplantation," Stem Cell Reports, 2014, vol. 2, No. 3, pp. 337-350.
Gitler et al., "Neurodegenerative disease: models, mechanisms, and a new hope," Available at Disease Models and Mechanisms (10); 499-502, 2017.
Kirkeby et al., "Generating Regionalized Neuronal Cells from Pluripotency, a Step-by_Step Protocol," Frontiers in Cellular Neuroscience, 2013, vol. 6, No. 64, pp. 1-4.
Kirkeby et al., "Generation of Regionally Specified Neural Progenitors and Functional Neurons from Human Embryonic Stem Cells under Defined Conditions," Cell Reports, 2012, vol. 1, No. 6, pp. 703-714.
Kirkeby et al., "Predictive markers guide differentiation to improve graft outcome in clinical translation of hESC-based therapy for Parkinson's disease," Cell: Stem Cell, 2017, vol. 20, No. 1, pp. 135-148.
Kriks et al., "Dopamine neurons derived from human ES cells efficiently engraft in animal models of Parkinson's disease," Research Letter, Dec. 22/29, 2011, vol. 480, Nature, 547-551, dol:10.1038/nature 10648.
Noibrant et al., "Generation of high-purity human vellral midbrain dopaminergic progenitors for in vitro maturation and intracerebral transplantation," Nature Protocols, 2017, vol. 12, No. 9, pp. 1962-1979.
Roussa et al., "TGF-beta promotes survival on mesenccephalic dopaminergic neurons in cooperation with Shh and FGF-8," Neurobiology of Disease, 2004, vol. 16, pp. 300-310.

(Continued)

Primary Examiner — Emily A Cordas
(74) Attorney, Agent, or Firm — Jianjie Hu

(57) ABSTRACT

The present disclosure relates to methods for producing dopaminergic cells and evaluating their functionality. When pluripotent human embryonic stem cells are cultured on plates coated with laminin-111, laminin-121, laminin-521, laminin-421, or laminin-511 in cell culture medium containing a GSK3 inhibitor and a TGF-β inhibitor as well as timely administered fibroblast growth factor, desired neural cells are produced at far higher rates. Useful cell culture kits for producing such dopaminergic cells are also described herein, as are methods of using such cells for stem cell therapy.

12 Claims, 25 Drawing Sheets

Specification includes a Sequence Listing.

(56) References Cited

OTHER PUBLICATIONS

Volkman et al., "Concise Review: Mesenchymal Stem Cells in Neurodegenerative Diseases," Stem Cells, 2017, vol. 35, pp. 1867-1880.

Xi et al., "Specification of midbrain dopamine neurons from primate pluripotent stem cells," Stem Cells, 2012, vol. 30, No. 8, pp. 1655-1663.

Yan et al., Directed differentiation of dopaminergic neuronal subtypes from human embryonic stem cells, Stem Cells, 2005, vol. 23, No. 6, pp. 781-790.

Yao et al., "Laminin regulates PDGFR?+ cell stemness and muscle development," Nature Communications, 2016, vol. 7, pp. 1-15.

Zhang et al., "Directed dopaminergic neuron differentiation from human pluripotent stem cells," Journal of Visualized Experiments, 2014, vol. 91, E51737, pp. 1-8.

Sundberg et al., "Improved cell therapy protocols for Parkinson's disease based on differentiation efficiency and safety of hESC-, hiPSC-, and non-human primate iPSC-derived dopaminergic neurons." Stem Cells. Aug. 2013, vol. 31, No. 8, pp. 1548-1562.

Menezes et al., "Polylaminin, a polymeric form of laminin, promotes regeneration after spinal cord injury," The FASEB Journal, Jul. 2010, vol. 24, No. 11, pp. 4513-4522.

Xi et al., "Specification of Midbrain Dopamine Neurons from Primate Pluripotent Stem Cells," Stem Cells, 2012, vol. 30, pp. 1655-1663.

Perrier et al., "Derivation of midbrain dopamine neurons from human embryonic stem cells," Proc Natl Acad Sci USA, Aug. 2004, vol. 101, No. 34, pp. 12543-12548.

\* cited by examiner

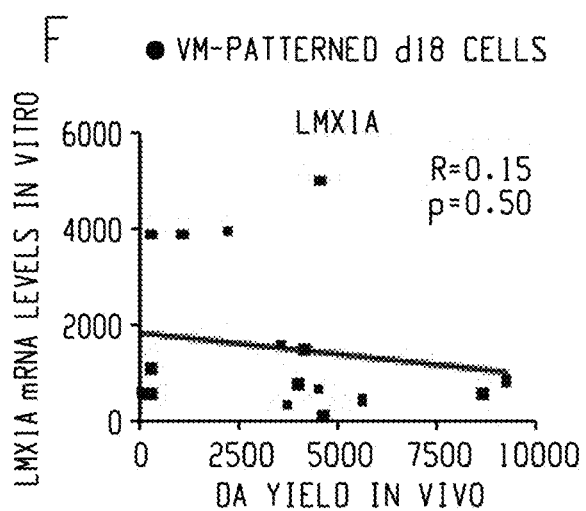
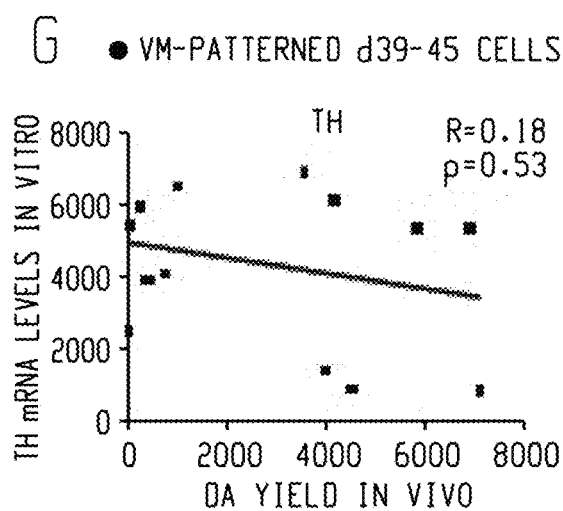
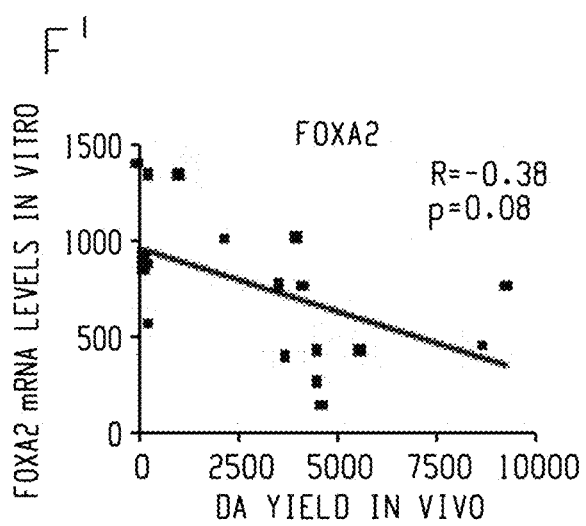
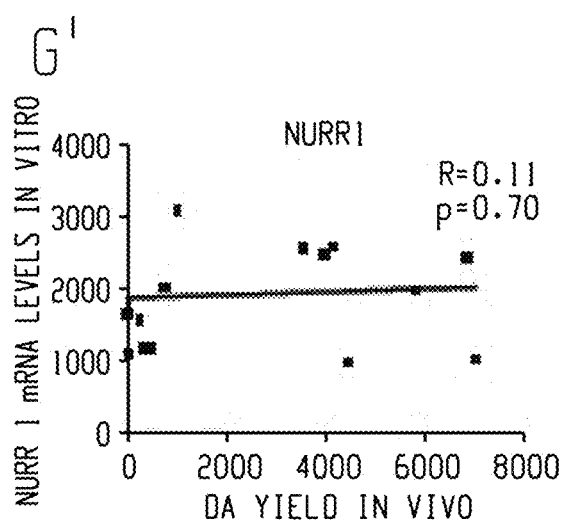
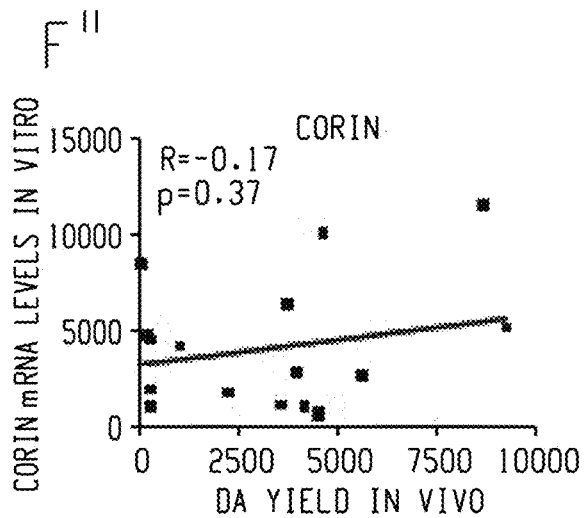
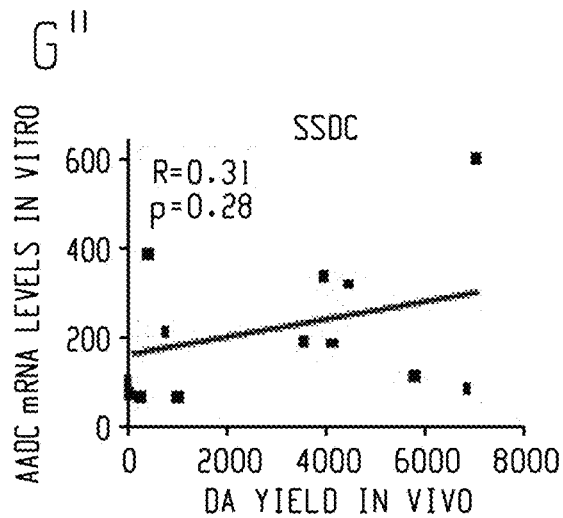
Fig. 4F
Fig. 4G

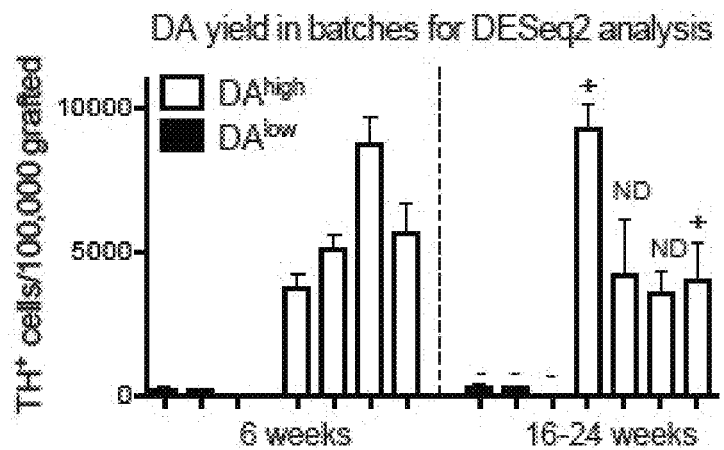
FIG. 5A
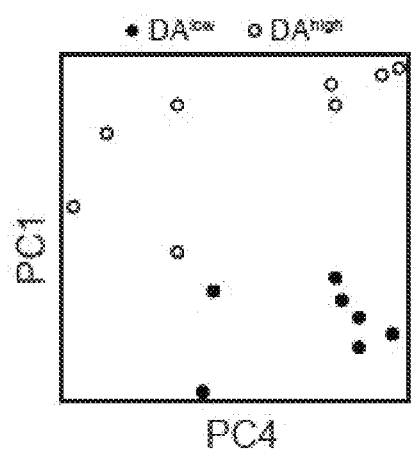
FIG. 5B
| Gene | log2 FC | Adj. p-value |
|---|---|---|
| FGF8 | 3.81 | 4.44E-13 |
| PAX5 | 3.45 | 2.75E-10 |
| CNPY1 | 2.89 | 3.50E-07 |
| FREM1 | 2.71 | 3.85E-10 |
| CSMD3 | 2.52 | 1.64E-05 |
| TAL2 | 2.45 | 3.14E-06 |
| EN2 | 2.41 | 1.02E-04 |
| EN1 | 2.38 | 1.65E-06 |
| MARCO | 2.33 | 1.69E-04 |
| SPRY1 | 2.32 | 1.08E-09 |
| PAX8 | 2.29 | 2.83E-04 |
| SLC30A3 | 2.26 | 3.29E-04 |
FIG. 5C
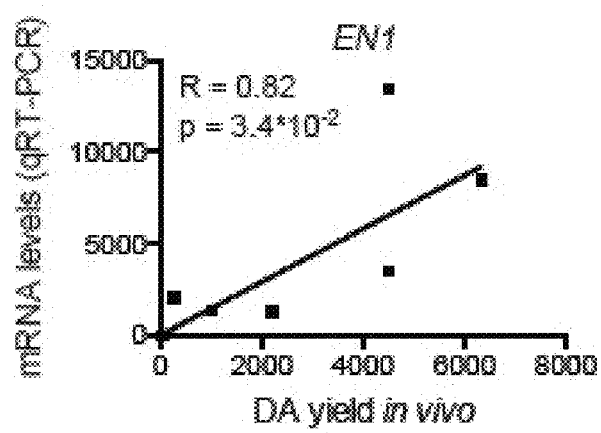
FIG. 5D

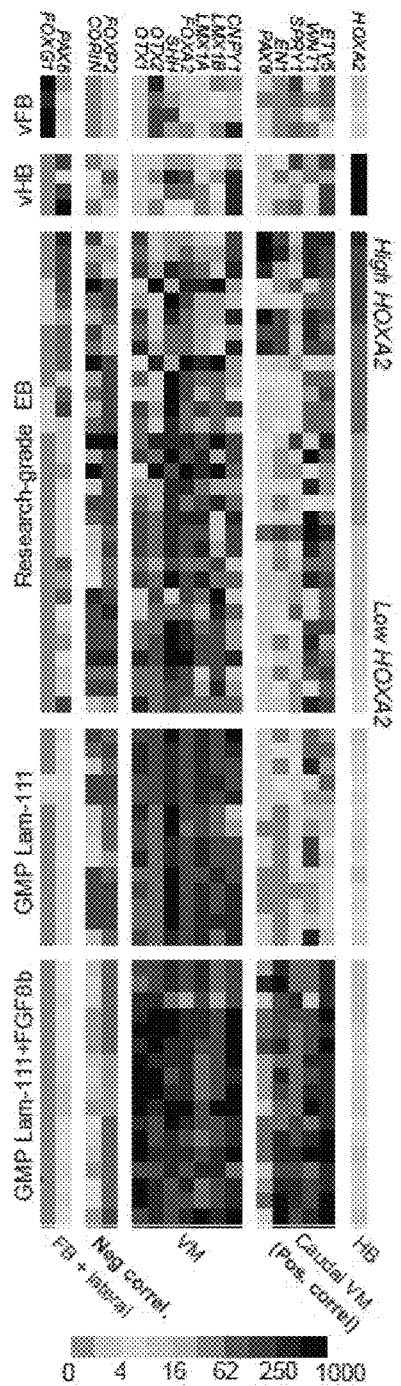
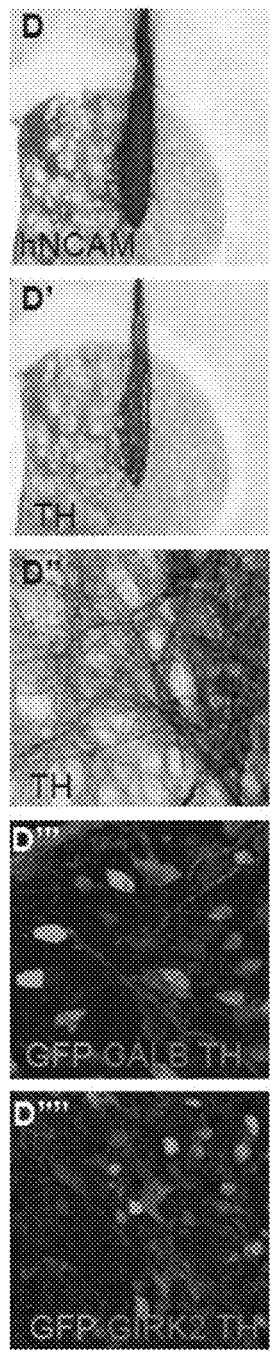
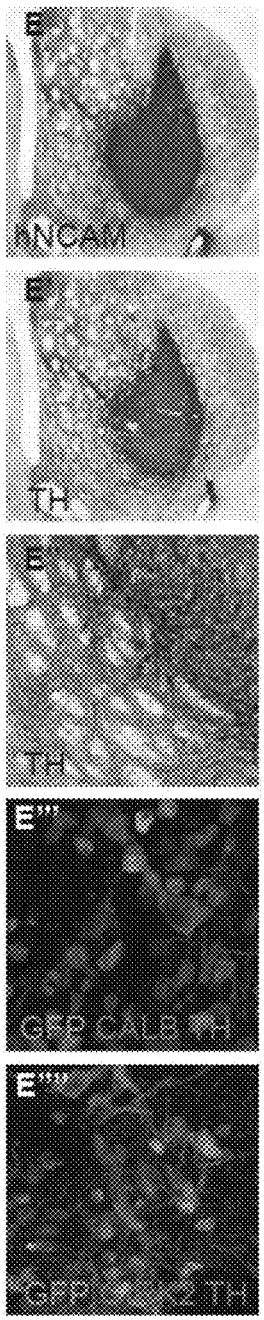
FIG. 9C
FIG. 9D
FIG. 9E

METHODS AND COMPOSITIONS FOR PRODUCING STEM CELL DERIVED DOPAMINERGIC CELLS FOR USE IN TREATMENT OF NEURODEGENERATIVE DISEASES

CROSS-REFERENCE TO RELATED APPLICATIONS

This application is a Divisional of application Ser. No. 15/093,927, filed Apr. 8, 2016, which claims priority to U.S. Provisional Patent Application Ser. No. 62/300,000, filed Feb. 25, 2016; and to U.S. Provisional Patent Application Ser. No. 62/182,051, filed Jun. 19, 2015; and to U.S. Provisional Patent Application Ser. No. 62/145,467, filed Apr. 9, 2015; the disclosures of which are hereby fully incorporated by reference.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, "180036US05_SeqList_ST25", which was created on May 17, 2019. The Sequence Listing is made up of 9 kilobytes, and the information contained in the attached "SEQUENCE LISTING" is identical to the information in the specification as originally filed. No new matter is added.

BACKGROUND

The present disclosure relates to methods for producing certain desired dopaminergic cells from human pluripotent stem cells (hESCs) and for predicting their phenotypic maturation after transplantation to the brain based on molecular markers. These dopaminergic cells can then be used in stem cell based therapies such as for treating neurodegenerative diseases including Parkinson's disease. Also disclosed are kits for practicing the methods. Very generally, the stem cells are cultured on a substrate of laminin-111 (or other recombinantly produced laminins) and exposed to a variety of cell culture mediums to produce the dopaminergic cells with much higher efficiency than previously attained.

Laminins are a family of heterotrimeric glycoproteins that reside primarily in the basal lamina. They function via binding interactions with neighboring cell receptors on the one side and by binding to other laminin molecules or other matrix proteins such as collagens, nidogens or proteoglycans. The laminin molecules are also important signaling molecules that can strongly influence cellular behavior and function. Laminins are important in both maintaining cell/tissue phenotype, as well as in promoting cell growth and differentiation in tissue repair and development.

Laminins are large, multi-domain proteins, with a common structural organization. A laminin protein molecule comprises one α-chain subunit, one β-chain subunit, and one γ-chain subunit, all joined together in a trimer through a coiled-coil domain. The twelve known laminin subunit chains can form at least 15 trimeric laminin types in native tissues. Within the trimeric laminin structures are identifiable domains that possess binding activity towards other laminin and basal lamina molecules, and membrane-bound receptors. FIG. 1 shows the three laminin chain subunits separately. For example, domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

There exist five different alpha chains, three beta chains and three gamma chains that in human tissues have been found in at least fifteen different combinations. These molecules are termed laminin-1 to laminin-15 based on their historical discovery, but an alternative nomenclature describes the isoforms based on their chain composition, e.g. laminin-111 (laminin-1) that contains alpha-1, beta-1 and gamma-1 chains. Four structurally defined family groups of laminins have been identified. The first group of five identified laminin molecules all share the β1 and γ1 chains, and vary by their α-chain composition (α1 to α5 chain). The second group of five identified laminin molecules, including laminin-521, all share the β2 and γ1 chain, and again vary by their α-chain composition. The third group of identified laminin molecules has one identified member, laminin-332, with a chain composition of α3β3γ2. The fourth group of identified laminin molecules has one identified member, laminin-213, with the newly identified γ3 chain (α2β1γ3).

Human embryonic stem (hES) cells hold promise for the development of regenerative medicine for a variety of diseases, such as spinal cord and cardiac injuries, type I diabetes and neurodegenerative disorders like Parkinson's Disease. A stem cell is an undifferentiated cell from which specialized cells are subsequently derived. Embryonic stem cells possess extensive self-renewal capacity and pluripotency with the potential to differentiate into cells of all three germ layers. They are useful for therapeutic purposes and may provide unlimited sources of cells for tissue replacement therapies, drug screening, functional genomics and proteomics.

Stem cell based therapies and treatments for neurodegenerative diseases are expected to reach clinical trials soon. However, a major hurdle remains in generating standardized good manufacturing practices (GMP)-grade human pluripotent stem (hPS) cell-based progenitors that upon transplantation will mature and function in the adult brain. As cells are transplanted as immature progenitors and full maturation into functionally integrated neurons requires 6 months or longer in vivo, transplanted cells cannot be assessed for functionality prior to transplantation, and there is a lack of markers that reliably predict yield and maturation of the immature progenitors.

As a surrogate for markers predicting functional properties, the field has relied upon assessing transplanted progenitors by expression of genes and proteins developmentally linked to the generation of certain neuronal subtypes. Since it is uncertain if these markers are predictive of terminal differentiation and functional maturation, the progenitors must therefore be taken through lengthy in vivo functional assessment in order to control for batch-to-batch variation and therapeutic efficacy. This can pose a significant hurdle for the generation of cells for larger cohorts of patients and for launching a standardized stem cell product to the clinic.

To reduce the in vivo studies needed to be performed during the cell developmental process, it will thus be necessary to identify a validated set of markers that can predict the in vivo performance of the stem cell product prior to transplantation. Being able to predict an in vivo graft outcome at the progenitor stage may also lead to the production of standardized cell products from variable input sources, such as from patient-derived cells or hPS cell banks with HLA-haplotyped donors.

Parkinson's disease is a particularly interesting target for stem cell based therapies due to the relatively focal degeneration of a specific type of mesencephalic dopamine (mesDA) neuron. Proof-of-concept that cell replacement therapy for Parkinson's disease can be successful has been obtained in a number of clinical trials using fetal cells.

Recent developments have resulted in a better understanding of the developmental and cellular ontogeny of mesDA neurons from the floor plate of the ventral mesencephalon, and this knowledge has materialized into research grade differentiation protocols that result in the formation of ventral mesencephalon progenitors from hPS cells. In contrast to older protocols, these dopaminergic neurons of ventral mesencephalon origin have been shown to survive, mature, and acquire appropriate functional properties in animal models of Parkinson's disease. Moreover, grafts generated from these protocols do not result in cell overgrowths or tumor formation, thus making them suitable candidate cells for stem cell replacement therapies.

In current ventral mesencephalon differentiation protocols, mesencephalic floor plate markers LMX1A, FOXA2, OTX2, and CORIN are commonly used to confirm the mesDA identity of progenitors in vitro prior to grafting, but a new study has revealed that these and several other commonly used ventral mesencephalon markers are also co-expressed in diencephalic progenitors of the subthalamic nucleus. Thus, they appear to be suboptimal markers in protocols for the generation of enriched mesDA neurons, as they are clearly not specific to the mesDA domain.

For the purposes of regenerative medicine and for modeling human neural cells, there is a desire to develop methods that allow derivation and culturing of pluripotent stem cells under chemically defined, xeno-free, pathogen-free, and for reproducible differentiation of these cells into neural cells with regenerative capacity. Desirably, such methods should provide large quantities of such differentiated cells. Further, it would be desirable to develop methods for predicting successful graft outcomes of transplanted progenitors in an animal model.

BRIEF DESCRIPTION

The present disclosure provides methods for producing certain stem cell derived desired dopaminergic cells as well as methods for evaluating their functionality after transplantation. These dopaminergic cells can then be used in stem cell based therapies such as for treating neurodegenerative diseases including Parkinson's disease. In further aspects, the present disclosure provides a kit for producing dopaminergic cells from embryonic stem cells.

The present disclosure also provides methods for culturing certain desired stem cells in monolayer cultures which facilitates cellular homogeneity, removal of the stem cells from a cell culture plate or other cellular support in single cell suspension, and replating stem cells in single cell suspension for passaging and expansion in significant dilutions that enable expansion of stem cell cultures and large scale production of such cells.

In some aspects, the disclosure describes the plating of pluripotent stem cells on a substrate of Laminin-111 or Laminin-121, and culturing the cells using several different cell culture mediums to obtain dopaminergic cells, particularly caudalized dopaminergic progenitor cells. The cells may be passaged with EDTA prior to plating.

In various embodiments, as many as six different cell culture mediums can be used. In others, only three or four different mediums need to be used.

The stem cells can be cultured in a primary medium comprising N2 medium (N2M), a TGF-β inhibitor, noggin, sonic hedgehog protein, and a GSK3 inhibitor. A ROCK inhibitor may be added to the medium for the first 24-72 hours The primary medium may then be removed and a secondary medium is added, the secondary medium comprising N2 medium and a fibroblast growth factor (FGF). The FGF can be FGF8b. The secondary medium may be added about 156 hours to about 228 hours after the plating.

The secondary medium can then be removed and the stem cells replated. The replating can occur about 252 hours to about 276 hours after the plating.

The replating can occur using a tertiary medium that comprises a B27 medium, a ROCK inhibitor, the FGF, a brain derived neurotrophic factor (BDNF), and ascorbic acid.

The stem cells may then be cultured in a quaternary medium, the quaternary medium comprising a B27 medium, the FGF, a brain derived neurotrophic factor (BDNF), and ascorbic acid. The stem cells can be cultured in the quaternary medium until about 372 hours to about 396 hours after the original plating (not the replating). Put another way, the replated stem cells are cultured in the quaternary medium for a time period of about 108 hours to about 132 hours.

In some other embodiments, the first medium includes a neural induction medium (NIM) or an N2 medium, a ROCK inhibitor, a TGFβ inhibitor, a GSK3 inhibitor, and optionally a sonic hedgehog protein and a noggin protein.

According to some embodiments, the second medium includes (i) NIM or an N2 medium; a TGF-β inhibitor, and a GSK3 inhibitor, and optionally a sonic hedgehog protein and a noggin protein. The second medium does not contain the ROCK inhibitor of the first medium. The second medium may be added about 36 hours to about 60 hours after plating.

According to some other embodiments, the third medium comprises a neural proliferation medium (NPM) and a TGF-β inhibitor; and optionally the GSK3 inhibitor and sonic hedgehog protein. The third medium may be added about 84 hours to about 108 hours after the first plating, and can be renewed about 156 hours to about 180 hours after the first plating. The third medium may be removed after about 156 hours to about 228 hours after the first plating.

In further embodiments, the fourth medium comprises (i) a neural proliferation medium (NPM) or an N2 medium; and (ii) a fibroblast growth factor (FGF). The fourth medium may be added about 156 hours to about 228 hours after the first plating. The fourth medium may be removed after about 36 hours to about 108 hours exposure, i.e. about 252 hours to about 276 hours after the original plating. The cells are then replated on a second plate coated with laminin-111, laminin-121, laminin-521, laminin-421, or laminin-511.

A fifth medium may be used that comprises a B27 medium; a brain derived neurotrophic factor (BDNF); ascorbic acid (AA); a glial cell line-derived neurotrophic factor (GDNF); and a fibroblast growth factor (FGF). The fifth medium can be renewed about 324 hours to about 348 hours after the original plating. After about 14 days to 16 days, i.e. about 336 hours to about 384 hours, the progenitor cells are obtained. If additional time is desired, a sixth cell culture medium can be used that comprises a B27 medium; a brain derived neurotrophic factor (BDNF); ascorbic acid (AA); a glial cell line-derived neurotrophic factor (GDNF), a cAMP agonist (e.g. dibutyryl-cAMP) and a gamma-secretase inhibitor (DAPT); and does not contain a fibroblast growth factor (FGF).

Also disclosed herein are methods for providing caudalized dopaminergic progenitor cells with a high probability of successful graft outcome, comprising: plating embryonic stem cells on a first substrate coated with laminin-111, laminin-121, laminin-521, laminin-421, or laminin-511 to produce dopaminergic progenitor cells; identifying dopaminergic progenitor cells that express caudal ventral midbrain markers; and isolating the identified dopaminergic progenitor cells from the other dopaminergic progenitor cells on the substrate to obtain the caudalized dopaminergic progenitor cells with a high probability of successful graft outcome.

The methods may further comprise grafting the caudalized dopaminergic progenitor cells into a brain of a mammal. The mammal can be a human. This grafting can be performed for the treatment of a neurodegenerative disease, such as Parkinson's disease.

The step of identifying ventral midbrain progenitors can be defined by co-expression of OTX2, FOXA2 and LMX1A/B. The step of identifying dopaminergic progenitor cells within the ventral midbrain domain can be performed by identifying cells that express high levels of EN1, SPRY1, WNT1, CNPY1, PAX8, ETV5, PAX5, FGF8, SP5, or TLE4. More particularly, the step of identifying dopaminergic cells can be performed by identifying cells that express high levels of EN1, SPRY1, PAX8, CNPY1, and ETV5.

The step of identifying dopaminergic progenitor cells within ventral midbrain cultures can further include excluding cells that express high levels of EPHA3, FEZF1, WNT7B, BARHL1, BARHL2, FOXG1, SIX3, HOXA2, GBX2, or PAX6 and by identifying cells that express only low to intermediate levels of CORIN and FOXP2.

The present disclosure also describes a kit for producing dopaminergic cells in vitro. The kit includes: a cell culture plate with a coating of laminin-111, laminin-121, laminin-521, laminin-421, or laminin-511; a cell culture medium; a GSK3 inhibitor; sonic hedgehog protein; a ROCK inhibitor; a TGF-β inhibitor; a fibroblast growth factor (FGF); a brain derived neurotrophic factor (BDNF); and ascorbic acid (AA).

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

FIGS. 4A-4G are a set images and graphs illustrating that batches of ventral mesencephalic-patterned hESCs give variable outcomes, which are not correlated with common mesDA markers. Thirty-three (33) groups of rats were subjected to one-sided dopaminergic lesions with 6-OHDA were grafted with 28 different batches of VM-patterned hESCs. All grafts were derived from H9 cells.

FIG. 4A is a set of images taken from selected animals after in vivo maturation. The brains were stained for TH (tyrosine hydroxylase) content, revealing varied outcomes of the grafts. FIG. 4B is a quantification of dopaminergic (DA) cell yield in individual animals across 33 batches. The y-axis is the number of TH+ cells per 100,000 cells transplanted, and runs from 0 to 20,000 in intervals of 4,000, then from 30,000 to 50,000 in intervals of 20,000 at the top. FIG. 4C is a quantification of graft volume in individual animals across 33 animal groups based on HuNu+ immunostainings. The y-axis is the graft volume in cubic millimeters per 100,000 cells transplanted, and runs from 0 to 7 in intervals of 1. FIG. 4D is a quantification of DA cell density (i.e. total TH+ cell number per $mm^3$ graft volume) in grafts from individual animals across 33 groups. The y-axis runs from 0 to 15,000 in intervals of 3,000. For FIGS. 4B-4D, cell content was normalized to 100,000 grafted cells, and horizontal bars indicate means for each batch. FIG. 4E is a schematic summary of the study of Example 6.

FIG. 4F is a graphic representation of gene expression of FOXA2, LMX1A and CORIN in the transplanted cell population on day 16 (day of transplantation) plotted versus the mean TH+ cell content (i.e. DA yield) in each graft experiment. For the LMX1A graph, the y-axis runs from 0 to 6,000 in intervals of 2,000, and the x-axis runs from 0 to 10,000 in intervals of 2,500. Spearman correlation: R=0.15, p=0.50. For the FOXA2 graph, the y-axis runs from 0 to 1,500 in intervals of 500, and the x-axis runs from 0 to 10,000 in intervals of 2,500. Spearman correlation: R=−0.38, p=0.08. For the CORIN graph, the y-axis runs from 0 to 15,000 in intervals of 5,000, and the x-axis runs from 0 to 10,000 in intervals of 2,500. Spearman correlation: R=−0.17, p=0.37.

FIG. 4G is a graphic representation of the gene expression of TH, NURR1 and AADC in the transplanted cell population on day 16 (day of transplantation) plotted versus the mean TH+ cell content (i.e. DA yield) in each graft experiment. Results from Spearman correlation analysis (ventral mesencephalic cells only) are given as R and p-values in each graph and tendencies of correlation are shown by linear regression lines. For the TH graph, the y-axis runs from 0 to 8,000 in intervals of 2,000, and the x-axis runs from 0 to 8,000 in intervals of 2,000. Spearman correlation: R=−0.18, p=0.53. For the NURR1 graph, the y-axis runs from 0 to 4,000 in intervals of 1,000, and the x-axis runs from 0 to 8,000 in intervals of 2,000. Spearman correlation: R=0.11, p=0.70. For the AADC graph, the y-axis runs from 0 to 600 in intervals of 200, and the x-axis runs from 0 to 8,000 in intervals of 2,000. Spearman correlation: R=0.31, p=0.28.

FIGS. 5A-5I are a set of images and graphs indicating that RNA sequencing analysis of transplanted cells reveals positive correlation between graft TH+ content and markers of the midbrain-hindbrain border (MHB). All grafts were derived from H9 cells. FIG. 5A is a graphical representation of DA yield divided into DA-high and DA-low groups at 6 weeks and >16 weeks. Only experiments with relevant day 16 RNA samples were categorized as either high or low. Dopaminergic function of the grafts was assessed in grafts with long-term maturation (>16 weeks) through amphetamine induced rotation ("−" indicates lack of functional recovery, "+" indicates functional recovery, ND indicates not determined). The y-axis is the number of TH+ cells per 100,000 cells grafted, and runs from 0 to 10,000 in intervals of 5,000. FIG. 5B is a PCA plot of results from RNA sequencing analysis of day 16 cell samples from a revealed clustering of DA-low and DA-high samples on the PC4 axis. FIG. 5C is a list of results from Deseq2 analysis of RNA sequencing data from the DA-high versus DA-low cell samples (see boxed data points in FIG. 5I below). The list shows the 12 genes with highest log 2 fold change (log 2 FC) and with a p-value of <0.001.

FIG. 5D is a graph of EN1 mRNA levels and FIG. 5E is a graph of PAX8 mRNA levels, both measured by qRT-PCR in day 16 transplanted cell batches. For the EN1 graph, the y-axis runs from 0 to 15,000 in intervals of 5,000, and the x-axis runs from 0 to 8,000 in intervals of 2,000. For the PAX8 graph, the y-axis runs from 0 to 150 in intervals of 50, and the x-axis runs from 0 to 8,000 in intervals of 2,000. For both FIGS. 5D-5E, Spearman correlation analysis is given as R and p-values in each graph and correlations are visualized with linear regression lines.

FIG. 5F is a graphical summary of RNA sequencing correlation analysis showing positive correlations between TH+ content, graft volume and TH+ density and RNA levels of MHB genes and common ventral mesencephalic markers. Positive correlation is defined by Spearman correlation analysis with p<0.05. Genes verified by qRT-PCR are shown in bold. FIG. 5G is a graphical representation of a Spearman distance analysis of RNA levels in cell batches, showing co-regulation of MHB genes, whereas FOXP2, FOXA2, LMX1B, CORIN, LMX1A, and OTX2 are uncoupled or negatively coupled to the MHB genes cluster. FIG. 5H shows five representative images of TH+ neurons from different cell batches with high expression of predictive markers revealing mature morphology of the grafted cells. Scale bar: 50 μm.

FIG. 5I is a graphical analysis of predictive markers following the Deseq2 analysis of RNA sequencing data from DA-high and DA-low cell samples. Markers were plotted based on log 2 fold change compared to mean of normalized counts. The box in this figure shows the genes listed in FIG. 5C above.

FIG. 6A is a set of three graphs showing negative correlation between RNA levels of the diencephalic markers FEZF1, WNT7B, and EPHA3 in transplanted cells (day 16) and TH+ content in grafts. For the FEZF1 graph, the y-axis runs from 0 to 8 in intervals of 2, and the x-axis runs from 0 to 10,000 in intervals of 2,500. R=−0.63, p=0.015. For the WNT7B graph, the y-axis runs from 0 to 0.6 in intervals of 0.2, and the x-axis runs from 0 to 10,000 in intervals of 2,500. Spearman correlation: R=−0.54, p=0.024. For the EPHA3 graph, the y-axis runs from 0 to 20 in intervals of 5, and the x-axis runs from 0 to 10,000 in intervals of 2,500. Spearman correlation: R=−0.63, p=0.015.

FIG. 6B is a set of images of immunostainings of ventral mesencephalic-patterned hESC cultures (day 16) revealing the presence of STN domain fates (BARHL1+/FOXA2+ and PITX2+/LMX1A/B+ cells). FIG. 6C is a schematic overview of expression domains in the diencephalic STN region and in lateral midbrain domains. FIG. 6D is a set of confocal images of an 18 week old graft showing the presence of BARHL1+/PITX2+ and BARHL1+/PITX2− cells. FIG. 6E is a set of example images of BARHL1+ cell content in grafts derived from cell batches with low (left) or high (right) BARHL1 RNA levels at the day of transplantation.

FIG. 6F is a set of graphical representations showing positive correlations between BARHL1 and BARHL2 RNA levels at the time of transplantation (qRT-PCR) and the number of BARHL1+ cells in the mature grafts. For the BARHL1 graph, the y-axis runs from 0 to 1500 in intervals of 500, and the x-axis runs from 0 to 15,000 in intervals of 5,000. Spearman correlation: R=0.89, p=0.03. For the BARHL2 graph, the y-axis runs from 0 to 5000 in intervals of 1000, and the x-axis runs from 0 to 15,000 in intervals of 5,000. Spearman correlation: R=0.89, p=0.03. For FIGS. 6A and 6F, results from Spearman correlation analysis are given as R and p-values in each graph, and correlations are visualized with linear regression lines.

FIG. 7A is a graphical representation of mRNA levels of FOXG1, SIX3, GBX2, and HOXA2 following qRT-PCR analysis (day 10) after differentiating hESCs treated with FGF8b from days 0-9. For the FOXG1 graph, the y-axis runs from 0 to 800 in intervals of 200. For the SIX3 graph, the y-axis runs from 0 to 1000 in intervals of 200. For the GBX2 graph, the y-axis runs from 0 to 150 in intervals of 50. For the HOXA2 graph, the y-axis runs from 0 to 300 in intervals of 100. For all four graphs, the x-axis indicates the amount of FGF8b, and is either 0, 100, or 300 ng/mL.

FIG. 7B is a set of four immunostaining images (day 16) revealing patches of PITX2+ and NKX2.1+ cells and patches of LMX1− cells in cultures treated with FGF8b from d0-9. FIG. 7C is a set of nine immunostaining images illustrating that LMX1+/FOXA2+ ventral mesencephalic phenotype is maintained in cultures treated with FGF8b from day 7-16 or 9-16. FIG. 7D is a set of six immunostaining images illustrating that day 16 cultures treated with FGF8b from day 9-16 have decreased levels of BARHL1+ and FOXA2 cells. FIG. 7E is a set of six immunostaining images illustrating that day 16 cultures treated with FGF8b from day 9-16 have decreased levels of PITX2 but increased levels of EN1 cells. FIG. 7F is a graphical quantification of FIGS. 7D-7E. The y-axis runs from 0 to 100% in intervals of 20. FIG. 7G is a graphical representation of mRNA levels at day 16 of FOXA2, LMX1A, OTX2, and EN1 following PCR analysis. The labels on the y-axis are, from bottom to top, 1, 4, 16, 64, 256, and 1024.

FIG. 7H is a FACS plots of control and FGF8b-treated ventral mesencephalic-patterned cultures (day 16) showing unchanged percentages of FOXA2+ progenitors. For VM, the values are 94.6±2.7% (mean±SEM). For VM+FGF8, the values are 95.4±1.3%. For control, the values are 0.3±0.2%, n=3. FIG. 7I is a FACS plot of control and FGF8b-treated ventral mesencephalic-patterned cultures (day 16) showing decreased percentages of CORIN+ progenitors. For VM, the values are 52.9±4.5%. For VM+FGF8, the values are 28.1±1.8%. For control, the value is 0.0%, n=3.

FIG. 8A is a set of seven images illustrating neural differentiation of hESCs on different laminin subtypes. FIG. 8B is a pair of images exhibiting how the culturing of hESCs on LN-111 in pluripotency medium resulted in detachment and formation of spheres, whereas pluripotent cells efficiently attached to the LN-521 matrix. FIG. 8C is a graph comparing the use of LN-111 coated substrates to LN-121 coated substrates, showing the yield of dopaminergic cells is about equal on either substrate. FIG. 8D is a set of four images illustrating that seeding of low density hESCs on LN-111 matrix in supplemented N2 medium resulted in confluent neuralized cultures after 7 days of differentiation. FIG. 8E is a graph of the downregulation of OCT4 and NANOG mRNA levels across three days of differentiation on LN-111. The y-axis runs from 0.0 to 1.0 in intervals of 0.2, and the x-axis runs from 0 to 3 in intervals of 1.

FIG. 8F is a graph of cell yield across different combinations of basic medium (DMEM/F12+ NEUROBASAL® with N2 supplement, N2 supplement, B27 supplement, and DMEM/F12+). The y-axis is cell count in millions on day 11, and runs from 0 to 200 in intervals of 50.

FIG. 8G is a graphical comparison of cell yield from research-grade EB-based protocol with the cell yield from the GMP-adapted LN-111 protocol shown in FIG. 2. The y-axis is cell count in millions, and runs from 0 to 500 in intervals of 100. FIGS. 8H-8K exhibit that terminal maturation (day 45) of ventral mesencephalic progenitors generated by the GMP protocol of FIG. 2 resulted in electrophysiologically active neurons. FIG. 8H is a graph showing representative trace of action potentials induced with depolarizing current injections. FIG. 8I is a graph illustrating that some ventral mesencephalic cells showed spontaneous postsynaptic currents indicative of synaptic integration in the dish.

FIG. 8J is a graphical example of rebound depolarization after brief membrane depolarization characteristic of dopaminergic phenotype. FIG. 8K is an inset showing respective trace from FIG. 8J on an expanded scale.

FIGS. 9A-9E is a set of images and graphs indicating that differentiation of hESCs from GMP-compatible protocol produces ventral mesencephalic cell batches with reproducibly high expression of predictive markers from the caudal ventral mesencephalon. FIG. 9A is a set of three immunostained images taken of cultures differentiated according to the GMP protocol, showing a very high overlap of LMX1A/FOXA2. FIG. 9B is a set of two FACS plots of OTX2/FOXA2 double-labelling by flow cytometry with mean (%)±SEM of replicate experiments (n=3). For both plots, the y-axis (OTX2-APC) is logarithmic, with the bottom value being $10^0$, and proceeding through $10^1$, $10^2$, $10^3$, $10^4$, $10^5$, $10^6$, and $10^7$. The x-axis (FOXA2-PE) is also logarithmic, with the leftmost value being 100, and proceeding through $10^2$, $10^4$, and $10^6$.

FIG. 9C is a graphical representation of gene expression levels in human ESCs differentiated according to either research-grade embryoid body protocol or GMP-grade LN-111 protocol. Differentiations towards ventral forebrain (vFB) and ventral hindbrain (vHB) were included as controls. Values are color-coded and normalized to sample with highest expression for each gene (=1000). FIGS. 9D-9E are 10 representative images of additional grafts from batches containing high levels of caudal VM markers. The images of FIG. 9D are of grafted H9 cells, and FIG. 9E shows RC17 cells, both generated via the GMP-grade protocol.

DETAILED DESCRIPTION

Figure 1:
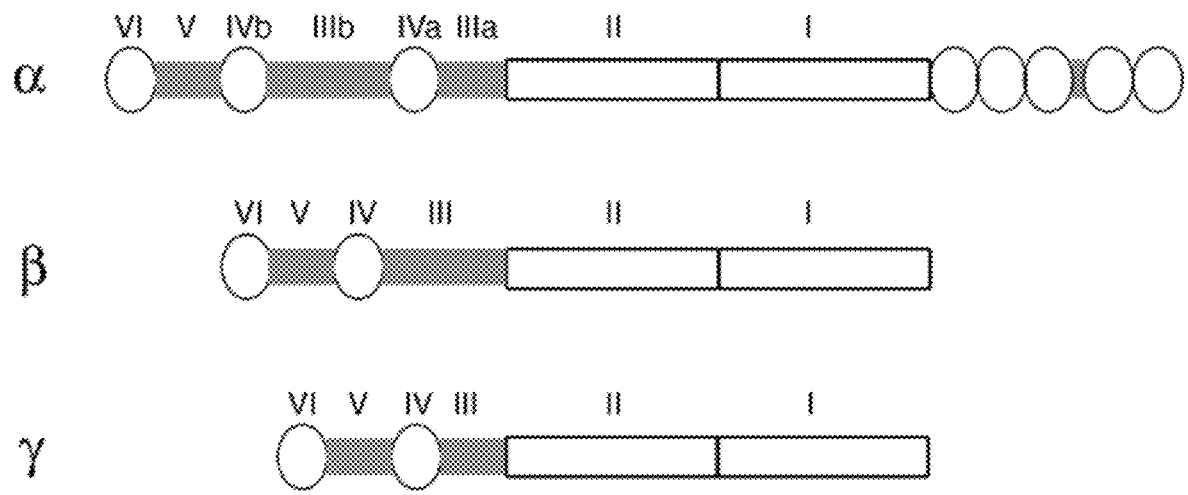
FIG. 1 shows the structural motifs of laminin alpha (α), beta (β), and gamma (γ) chains. The N-terminal, internal, and C-terminal globular domains are depicted as white ovals. The coiled-coil forming domains (I and II) are shown as white rectangles. The rod-like structures (domains V, IIIb, and IIIa) are depicted as grey rectangles.

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

Several well-known references that may be relevant to the present disclosure include: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, Second Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), or the Ambion 1998 Catalog (Ambion, Austin, Tex.).

As used herein, the term "laminin-521" refers to the protein formed by joining α5, β2 and γ1 chains together. The term should be construed as encompassing both recombinant laminin-521 and heterotrimeric laminin-521 from naturally occurring sources.

As used herein, the term "laminin-111" refers to the protein formed by joining α1, β1 and γ1 chains together. The term should be construed as encompassing both recombinant laminin-111 and heterotrimeric laminin-111 from naturally occurring sources.

As used herein, the term "laminin-121" refers to the protein formed by joining α1, β2 and γ1 chains together. The term should be construed as encompassing both recombinant laminin-121 and heterotrimeric laminin-121 from naturally occurring sources.

As used herein, the term "laminin-421" refers to the protein formed by joining α4, β2 and γ1 chains together. The term should be construed as encompassing both recombinant laminin-421 and heterotrimeric laminin-421 from naturally occurring sources.

As used herein, the term "laminin-511" refers to the protein formed by joining α5, β1 and γ1 chains together. The term should be construed as encompassing both recombinant laminin-511 and heterotrimeric laminin-511 from naturally occurring sources.

The term "intact" refers to the protein being composed of all of the domains of the α-chain, β-chain, and γ-chain, with the three chains being joined together to form the heterotrimeric structure. The protein is not broken down into separate chains, fragments, or functional domains. The term "chain" refers to the entirety of the alpha, beta, or gamma chain of the laminin protein. The term "fragment" refers to any protein fragment which contains one, two, or three functional domains that possesses binding activity to another molecule or receptor. However, a chain should not be considered a fragment because each chain possesses more than three such domains. Similarly, an intact laminin protein should not be considered a fragment. Examples of functional domains include Domains I, II, III, IV, V, VI, and the G domain.

As used herein, the term "self-renewal" refers to the ability of the stem cell to go through numerous cycles of cell division and remain undifferentiated (i.e. pluripotent). Pluripotency itself refers to the ability of the stem cell to differentiate into any cell type. The term "proliferation" refers to the ability of the stem cell to divide. Survival refers to the ability of the stem cell to live, whether differentiated or undifferentiated, and does not require the stem cell to maintain its ability to divide or to differentiate.

The abbreviation "DA" refers to dopamine. It is generally used herein to refer to cells that can produce dopamine or to cells that can give rise to dopamine-producing cells.

The combination of the laminin substrate with the cell culture medium of the present disclosure results in a cell culture system that provides clinical grade dopaminergic cells. Particularly the method discloses more dopaminergic cells The present disclosure relates to more efficient methods of culturing stem cells to obtain differentiated neural cells for regenerative therapies. In particular, a laminin is used as a matrix/substrate for pluripotent stem cells, resulting in more differentiated cells than cultures containing alternative matrices. Only one laminin may be used as the matrix/substrate, or the matrix/substrate can include specific laminins, which are laminin-111 (LN-111), LN-121, LN-521, LN-421, or LN-511. Laminin-111 can normally be found in the epithelia and dermal papillae, endothelial cells, pancreas, peripheral nerves, and placenta.

The present disclosure also relates to different cell culture mediums that are used to provide nutrition to cells, particularly stem cells. In this regard, stem cells typically require two things to be cultured: (1) a substrate or coating that provides a structural support for the stem cell; and (2) a cell culture medium to provide nutrition to the stem cell. The substrate or coating (1) is generally placed on, for example, a petri dish or some other container. Application of different cell culture mediums at appropriate time intervals in combination with a laminin-111 substrate result in a larger number of differentiated neural cells that produce dopamine (i.e. dopaminergic cells).

The stem cells that can be used with the methods and materials disclosed herein can be induced pluripotent stem cells, embryonic stem cells, adult stem cells, fetal stem cells, amniotic stem cells, and generally any pluripotent stem cell.

The methods can be modified to obtain neural cells of many different phenotypes. These neural cells can be used for stem cell based therapies, including being transplanted and grafted into the brain of a mammalian patient to treat various neurodegenerative diseases. In the absence of patterning factors, neural cells of a telencephalic fate are obtained. Rostro-caudal and dorsal-central patterning of neural progenitors can be controlled by a dose-dependent addition of patterning factors. These methods are described with reference to FIG. 2, which provides a timeline and a listing of the various ingredients in the cell culture mediums disclosed herein. As seen here, pluripotent stem cells are seeded on plates coated with laminin-111 and are cultured over a period of 16 days. The culturing media may contain various combinations of medium, differentiation factors, and patterning factors administered at specific intervals over a 16-25 day period.

Initially, four different cell culture mediums are illustrated, which are modified by the addition of differentiation factors and/or patterning factors to arrive at multiple different cell culture mediums. Those four mediums are referred to herein as neural induction medium (NIM), N2 medium (N2M), neural proliferation medium (NPM), and B27 medium (B27M).

The NIM, N2M, NPM, and B27M are made from a set of common ingredients. These common ingredients include DMEM/F12 medium, which is commercially available from Invitrogen (catalog nos. 10565 and 21331). DMEM/F12 generally contains the following ingredients listed in Table 1:

TABLE 1

| DMEM/F12 Ingredients | Concentration (ng/mL) |
|---|---|
| Glycine | 187.5 |
| L-Alanine | 44.5 |
| L-Arginine hydrochloride | 1475 |
| L-Asparagine-H$_2$O | 75 |

TABLE 1-continued

| DMEM/F12 Ingredients | Concentration (ng/mL) |
|---|---|
| L-Aspartic acid | 66.5 |
| L-Cysteine hydrochloride-$H_2O$ | 175.6 |
| L-Cystine 2HCl | 312.9 |
| L-Glutamic Acid | 73.5 |
| L-Glutamine | 3650 |
| L-Histidine hydrochloride-$H_2O$ | 314.8 |
| L-Isoleucine | 544.7 |
| L-Leucine | 590.5 |
| L-Lysine hydrochloride | 912.5 |
| L-Methionine | 172.4 |
| L-Phenylalanine | 354.8 |
| L-Proline | 172.5 |
| L-Serine | 262.5 |
| L-Threonine | 534.5 |
| L-Tryptophan | 90.2 |
| L-Tyrosine disodium salt dihydrate | 557.9 |
| L-Valine | 528.5 |
| Biotin | 0.035 |
| Choline chloride | 89.8 |
| D-Calcium pantothenate | 22.4 |
| Folic Acid | 26.5 |
| Niacinamide | 20.2 |
| Pyridoxine hydrochloride | 20 |
| Riboflavin | 2.19 |
| Thiamine hydrochloride | 21.7 |
| Vitamin $B_{12}$ | 6.8 |
| i-Inositol | 126 |
| Calcium Chloride ($CaCl_2$) (anhyd.) | 1166 |
| Cupric sulfate ($CuSO_4$—$5H_2O$) | 0.013 |
| Ferric Nitrate ($Fe(NO_3)_3$—$9H_2O$) | 0.5 |
| Ferric sulfate ($FeSO_4$—$7H_2O$) | 4.17 |
| Magnesium Chloride (anhydrous) | 286.4 |
| Magnesium Sulfate ($MgSO_4$) (anhyd.) | 488.4 |
| Potassium Chloride (KCl) | 3118 |
| Sodium Bicarbonate ($NaHCO_3$) | 24380 |
| Sodium Chloride (NaCl) | 69955 |
| Sodium Phosphate dibasic ($Na_2HPO_4$) anhydrous | 710.2 |
| Sodium Phosphate monobasic ($NaH_2PO_4$—$H_2O$) | 625 |
| Zinc sulfate ($ZnSO_4$—$7H_2O$) | 4.32 |
| D-Glucose (Dextrose) | 31510 |
| Hypoxanthine Na | 23.9 |
| Linoleic Acid | 0.42 |
| Lipoic Acid | 1.05 |
| Phenol Red | 81 |
| Putrescine 2HCl | 0.81 |
| Sodium Pyruvate | 550 |
| Thymidine | 3.65 |

Another common ingredient is NEUROBASAL® medium, which is commercially available as MACS® neuro medium from Miltenyi (catalog no. 130-093-570) or from Life Technologies (catalog no. 13712-01). N2 supplement is commercially available from Life Technologies (catalog no. A13707-01) in 100× concentration. B27 supplement without vitamin A can be obtained from Life Technologies (catalog no. 12587-010) or as MACS® NEUROBREW®-21 from Miltenyi (catalog no. 130-097-263).

The NIM, N2M, NPM, and B27M mediums are made by mixing parts by volume of these common ingredients with other additives.

The neural induction medium (NIM) is formed from 1 part by volume (pbv) of a 50:50 mixture of DMEM/F12: NEUROBASAL®; 1 part of 1×N2 supplement (1:100); and 1 part of 1×B27 supplement (1:50); with addition of 2 mM L-glutamine and optionally 0.2% penicillin/streptavidin if needed.

The N2 medium (N2M) is formed from 1 part by volume (pbv) of a 50:50 mixture of DMEM/F12: NEUROBASAL®; and 1 part of 1×N2 supplement; with addition of 2 mM L-glutamine and optionally 0.2% penicillin/streptavidin if needed. In comparison to the NIM, the N2M does not contain B27 supplement at all.

The neural proliferation medium (NPM) is formed from 1 part of the 50:50 mixture of DMEM/F12: NEUROBASAL®; 1 part of 0.5×N2 supplement (1:200); and optionally 1 part of 0.5×B27 supplement (1:100); with addition of 2 mM L-glutamine and optionally 0.2% penicillin/streptavidin if needed. The N2 and B27 supplements are more diluted in the NPM compared to the NIM and the B27M. When B27 is present, this may be referred to as NPM-B.

The B27 medium (B27M) is formed from 1 part of NEUROBASAL® medium; and 1 part of 1×B27 supplement (1:50); with addition of 2 mM L-glutamine and optionally 0.2% penicillin/streptavidin if needed. The B27M does not contain N2 supplement at all.

The differentiation factors used in the present disclosure include a TGFβ inhibitor; recombinant human noggin; a brain derived neurotrophic factor (BDNF); ascorbic acid (AA); a glial cell line-derived neurotrophic factor (GDNF); a cyclic adenosine monophosphate (cAMP) such as dibutyryl-cyclic adenosine monophosphate (db-cAMP); and a gamma-secretase inhibitor such as DAPT. In particular embodiments, the TGFβ inhibitor is SB431542 (CAS #301836-41-9). Noggin can be obtained from R&D Systems (catalog no. 6057-GMP) or Miltenyi (catalog no. 130-103-456). BDNF (catalog no. 130-096-286) and GDNF (catalog no. 130-098-449) can be obtained from Miltenyi.

The patterning factors used in the present disclosure include a GSK3 inhibitor, fibroblast growth factor (FGF), and sonic hedgehog protein. In particular embodiments, the GSK3 inhibitor is CHIR99021 (CAS #252917-06-9). In other particular embodiments, the fibroblast growth factor is FGF8b. In yet other embodiments, the particular sonic hedgehog protein is SHH-C24II.

In particular embodiments, a ROCK inhibitor may be used for certain portions of the methods. The ROCK inhibitor may be Y27632 (CAS #129830-38-2). Noggin protein and a gamma-secretase, such as DAPT, can also be used.

Next, prior to differentiation, cells may be maintained on CELLSTART™ or laminin-521 in STEMPRO® medium or iPSBrew (catalog number 130-104-368). The cells may also be passaged with EDTA 4 to 6 days before initiation of differentiation. Healthy pluripotent stem cells should be used.

Figure 2:
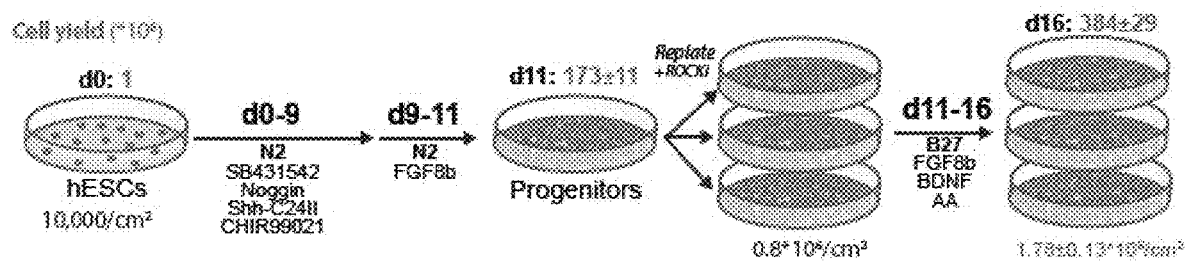
FIG. 2 is a graphic representation of some methods of the present disclosure, identifying specific ingredients and when they are applied to the stem cells to achieve the desired effect. This is a GMP-suitable differentiation protocol.
Figure 3:
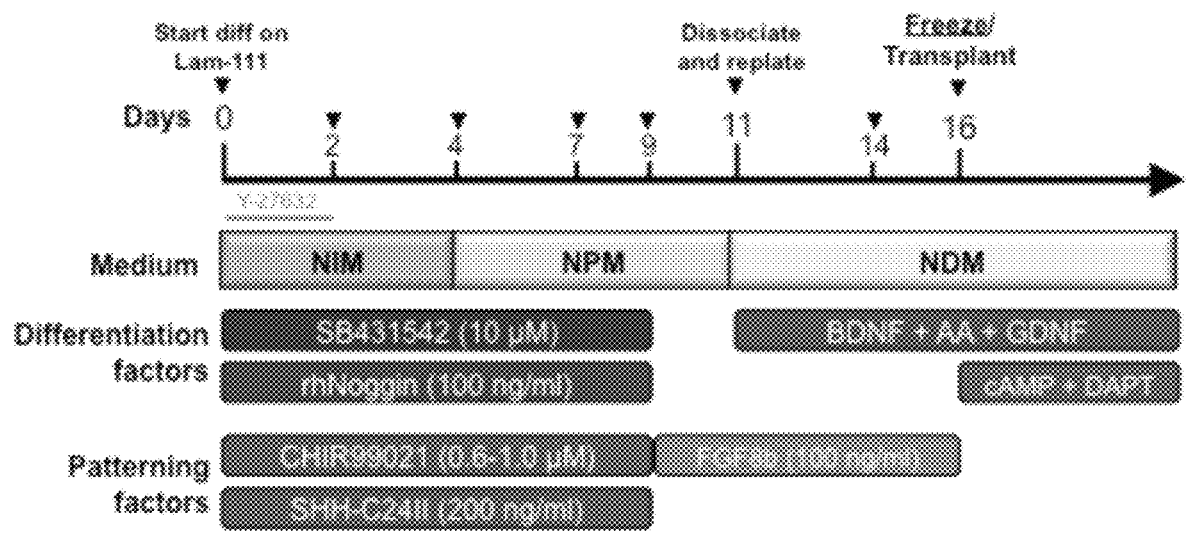
FIG. 3 is another graphic presentation of other methods of the present disclosure, in which alternative cell culture media (NIM and NPM) are used. NDM medium in this figure is equivalent to B27M

Referring now to FIG. 2 and FIG. 3, the differentiation protocol begins on Day 0, and continues for 16 days. After 16 days, the cells can be prepared for transplantation. On Day 0, the pluripotent stem cells are plated onto a substrate of laminin-111, LN-121, LN-521, LN-421, and/or LN-511. The substrate may consist entirely of laminin-111, entirely of LN-121, or be a combination of LN-111 and LN-121, or a combination of the other named laminins as well. The substrate may also include other basal factors. In particular embodiments, the laminin(s) consists of intact laminin, i.e. containing the entirety of all three chains. It is also contemplated that the substrate could consist of fragments of the specified laminin(s) in other particular embodiments. The stem cells can be plated at a density of about 10,000 cells per $cm^2$.

At least two different protocols/methods for differentiating the stem cells on the laminin-coated substrate during this 16-25 day period are contemplated herein. One protocol is illustrated in FIG. 2, and the other protocol is illustrated in FIG. 3.

In the protocol of FIG. 2, four different cell culture mediums are applied to the stem cells. The composition of those four cell culture mediums is now described. These cell culture mediums are referred to herein as a primary cell culture medium, a secondary cell culture medium, a tertiary cell culture medium, and a quaternary cell culture medium.

The primary cell culture medium comprises the N2M, a TGF-β inhibitor; and a GSK3 inhibitor. No B27 supplement is present. In particular embodiments, the primary cell culture medium consists of these listed ingredients. The TGF-β inhibitor is present in a concentration of about 5 μM to about 15 μM, and in particular about 10 μM. In specific embodiments, the TGF-β inhibitor is SB431542. The GSK3 inhibitor is present in a concentration of about 0.2 μM or greater. In specific embodiments, the GSK3 inhibitor is CHIR99021. In some embodiments, the primary cell culture medium further comprises a sonic hedgehog (SHH) protein, such as SHH-C24II. When present, the SHH protein is present in an amount of at least 50 ng/ml, including about 100 ng/ml to about 400 ng/ml, and in particular about 200 ng/ml. Noggin may also be present in an amount of about 50 ng/ml to about 150 ng/ml, and in particular about 100 ng/ml. Noggin also acts as a TGF-β inhibitor. In additional particular embodiments, the primary cell culture medium consists of these listed ingredients (including the SHH and the noggin). A ROCK inhibitor is present in the medium for the first 24 hours to 72 hours after plating. In specific embodiments the ROCK inhibitor is Y-27632. The ROCK inhibitor is present at a concentration of about 5 μM to about 15 μM, and in particular about 10 μM. If desired, the primary cell culture medium containing the ROCK inhibitor ("primary-A") can be considered a different medium from the primary cell culture medium that does not contain the ROCK inhibitor ("primary-B").

The secondary cell culture medium comprises the N2M and a fibroblast growth factor (FGF). In particular embodiments, the secondary cell culture medium consists of these listed ingredients. No B27 supplement is present. The FGF is present in an amount of about 50 ng/ml to about 150 ng/ml, and in particular about 100 ng/ml. In particular embodiments, the fibroblast growth factor is FGF8b.

The tertiary cell culture medium comprises the B27M, a ROCK inhibitor, a fibroblast growth factor (FGF), a brain derived neurotrophic factor (BDNF), and ascorbic acid (AA), and optionally a glial cell-line derived neurotrophic factor (GDNF). Please note that B27 is present in this medium, but N2 is not present. In particular embodiments, the tertiary cell culture medium consists of these listed ingredients. The FGF is present in an amount of about 50 ng/ml to about 150 ng/ml, and in particular about 100 ng/ml. In particular embodiments, the fibroblast growth factor is FGF8b. The BDNF is present in an amount of about 5 ng/ml to about 30 ng/ml, and in particular about 20 ng/ml. The AA is present in a concentration of about 0.1 mM to about 0.5 mM, and in particular about 0.2 mM. The ROCK inhibitor is present in a concentration of about 5 μM to about 15 μM, and in particular about 10 μM. The GDNF can be present in an amount of about 2 ng/ml to about 20 ng/ml, and in particular about 10 ng/ml, but is usually excluded.

The quaternary cell culture medium comprises the B27M, a fibroblast growth factor (FGF), a brain derived neurotrophic factor (BDNF), and ascorbic acid (AA), and optionally a glial cell-line derived neurotrophic factor (GDNF). Please note that B27 is present in this medium, but N2 is not present. In particular embodiments, the quaternary cell culture medium consists of these listed ingredients. The FGF is present in an amount of about 50 ng/ml to about 150 ng/ml, and in particular about 100 ng/ml. In particular embodiments, the fibroblast growth factor is FGF8b. The BDNF is present in an amount of about 5 ng/ml to about 30 ng/ml, and in particular about 20 ng/ml. The AA is present in a concentration of about 0.1 mM to about 0.5 mM, and in particular about 0.2 mM. The GDNF can be present in an amount of about 2 ng/ml to about 20 ng/ml, and in particular about 10 ng/ml, but is usually excluded. The quaternary cell culture medium is generally identical to the tertiary cell culture medium, but does not contain ROCK inhibitor.

Next, the differentiation protocol of FIG. 2 is described. The stem cells can be plated at a density of about 10,000 cells per cm$^2$. After the stem cells are originally plated on the laminin-coated substrate (as described above), the primary cell culture medium is applied for a period of about 156 hours to about 228 hours (i.e. about 7 days to about 9 days). The primary cell culture can be periodically renewed. The primary cell culture medium is then removed, and the secondary cell culture medium is added to the substrate.

In this regard, the secondary cell culture medium contains FGF, and different amounts of the FGF and timing of the FGF addition (i.e. 7-9 days) can control the rostral-caudal patterning of the resulting cells. The secondary cell culture medium is then removed about 252 hours to about 276 hours after the original plating (i.e. about 11 days). Put another way, the cells are exposed to the secondary cell culture medium for a period of about 36 hours to about 60 hours (i.e. about 2 to 4 days).

The cells are then replated through dissociation to single cells, and exposed to the tertiary cell culture medium which contains the ROCK inhibitor. The cell density at replating may be about 0.5 million cells per cm$^2$ to about 1 million cells per cm$^2$. It is contemplated that the tertiary cell culture medium is used for only a short period of time, i.e. about 48 hours or less, during the replating. The cells are then exposed to the quaternary cell culture medium until about 324 hours to about 396 hours (i.e. about 14-16 days) after the original plating. Put another way, the cells are exposed to the quaternary cell culture medium for a period of about 108 hours to about 132 hours (i.e. about 5 days). After about 14-16 days, the cell density may be as high as about 1.78 million cells per cm$^2$. After about 16 days to about 25 days, the neural cells are ready for cryopreservation or transplantation. The identity of the desired cells can be verified by expression of desired markers, as described further herein.

Referring now to FIG. 3, six different cell culture mediums are applied to the stem cells and the laminin-coated substrate during this 25-day period. The composition of those six cell culture mediums are now described.

The first cell culture medium comprises the NIM or the N2M; a ROCK inhibitor; a TGFβ inhibitor; and a GSK3 inhibitor. In particular embodiments, the first cell culture medium consists of these listed ingredients. The various additives may be any combination of the specific additives previously described above. The ROCK inhibitor is present in a concentration of about 5 μM to about 15 μM, and in particular about 10 μM. The TGFβ inhibitor is present in a concentration of about 5 μM to about 15 μM, and in particular about 10 μM. The GSK3 inhibitor is present in a concentration of about 0.2 μM or greater. As will be explained further herein, the amount/concentration of the GSK3 inhibitor will affect the type of neural cell that is obtained. In some embodiments, the first cell culture medium further comprises a sonic hedgehog (SHH) protein. When present, the SHH protein is present in an amount of at least 50 ng/ml, including about 100 ng/ml to about 300 ng/ml, and in particular about 200 ng/ml. Noggin may also be present in an amount of about 50 ng/ml to about 150 ng/ml, and in particular about 100 ng/ml. Noggin also acts as a TGFβ inhibitor. In additional particular embodiments, the first cell culture medium consists of these listed ingredients (including the SHH and the noggin).

The second cell culture medium comprises the NIM or the N2M; a TGFβ inhibitor; and a GSK3 inhibitor; but does not contain the ROCK inhibitor that was present in the first cell culture medium. In particular embodiments, the second cell culture medium consists of these listed ingredients. The amounts of these additives are as described above. In some embodiments, the second cell culture medium further comprises a sonic hedgehog (SHH) protein. When present, the SHH protein is present in an amount of at least 50 ng/ml, including about 100 ng/ml to about 300 ng/ml, and in particular about 200 ng/ml. Noggin may also be present in an amount of about 100 ng/ml to about 300 ng/ml in this second cell culture medium, and in particular about 200 ng/ml. In particular embodiments, the second cell culture medium consists of these listed ingredients (including the SHH and the noggin).

The third cell culture medium comprises (i) the NPM or the N2M; and (ii) a TGFβ inhibitor. The TGFβ inhibitor is present in a concentration of about 5 μM to about 15 μM, and in particular about 10 μM. Noggin may also be present in an amount of about 50 ng/ml to about 150 ng/ml, and in particular about 100 ng/ml. In some embodiments, the third cell culture medium further comprises a GSK3 inhibitor and SHH protein. When present, the GSK3 inhibitor is present in a concentration of about 0.2 μM or greater. When present, the SHH protein is present in an amount of at least 50 ng/ml, including about 100 ng/ml to about 300 ng/ml, and in particular about 200 ng/ml. In particular embodiments, the third cell culture medium consists of the NPM or N2M, TGFβ inhibitor, GSK3 inhibitor, and SHH protein.

The fourth cell culture medium comprises (i) the NPM or the N2M; and (ii) a FGF. The FGF is present in an amount of about 50 ng/ml to about 150 ng/ml, and in particular about 100 ng/ml.

The fifth cell culture medium comprises the B27M; a brain derived neurotrophic factor (BDNF); ascorbic acid (AA); a glial cell line-derived neurotrophic factor (GDNF); and a FGF. In particular embodiments, the fifth cell culture medium consists of these listed ingredients. The BDNF is present in an amount of about 5 ng/ml to about 30 ng/ml, and in particular about 20 ng/ml. The AA is present in a concentration of about 0.1 mM to about 0.5 mM, and in particular about 0.2 mM. The GDNF is present in an amount of about 2 ng/ml to about 20 ng/ml, and in particular about 10 ng/ml. The FGF is present in an amount of about 50 ng/ml to about 150 ng/ml, and in particular about 100 ng/ml.

The sixth cell culture medium can be used for neuronal maturation; and comprises the B27M; a BDNF; ascorbic acid (AA); a GDNF; db-cAMP; and a gamma-secretase. In particular embodiments, the sixth cell culture medium consists of these listed ingredients. The BDNF is present in an amount of about 5 ng/ml to about 30 ng/ml, and in particular about 20 ng/ml. The AA is present in a concentration of about 0.1 mM to about 0.5 mM, and in particular about 0.2 mM. The GDNF is present in an amount of about 2 ng/ml to about 20 ng/ml, and in particular about 10 ng/ml. The db-cAMP is present in a concentration of about 200 μM to about 800 mM, and in particular about 500 μM. The gamma-secretase is present in a concentration of about 0.1 μM to about 5 μM, and in particular about 1 μM.

After the stem cells are originally plated on the laminin-coated substrate, the first cell culture medium is applied for a period of about 36 hours to about 60 hours, and in particular for about 48 hours (i.e. 2 days). The first cell culture medium is then removed, and the second cell culture medium is added to the substrate. The second cell culture medium is removed about 84 hours to about 108 hours after the original plating (i.e. about day 4), and is replaced with the third cell culture medium. The third cell culture medium can be renewed about 156 hours to about 180 hours after the original plating. The third cell culture medium is then removed about 156 hours to about 228 hours after the original plating (i.e. about 7-9 days after original plating).

In this regard, rostro-caudal patterning of the resulting cells can be controlled by dose-dependent addition of the GSK3 inhibitor during this initial period using the first through third cell culture mediums. In some embodiments, 0.2 μM to 0.4 μM of the GSK3 inhibitor are used in these cell culture mediums for diencephalic fates. In other embodiments, 0.6 μM to 0.8 μM of the GSK3 inhibitor may be used for mesencephalic fates. In yet other embodiments, 1 μM to 2 μM of the GSK3 inhibitor may be used for anterior rhomencephalic fates. In yet further embodiments more than 4 μM of the GSK3 inhibitor may be used for posterior rhomencephalic fates.

Similarly, dorso-ventral patterning of neural progenitors can be controlled by dose-dependent addition of the SHH protein. In some embodiments, if no SHH protein is added to the culture, the cells will be enriched for alar plate fates. In other embodiments, about 50 ng/ml to about 150 ng/mL SHH protein may be added to enrich for basal plate fates. In yet other embodiments, more than 200 ng/mL SHH protein may be added to enrich for floor plate fates. To enrich for roof plate fates, no TGFβ inhibitor or noggin should be present in the third cell culture medium (applied about Day 4). This allows for activation of bone morphogenic protein (BMP).

In some embodiments, purmorphamine and SHH protein may be added to the second and third cell culture mediums to obtain more potent ventralization. The purmorphamine should be present in a concentration of about 0.1 μM to about 1 μM, and in particular about 0.5 mM.

Continuing on, the third cell culture medium is substituted with the fourth cell culture medium after about 156 hours to about 228 hours after the original plating. As discussed above, the amount and timing of the FGF in the fourth cell culture medium can control rostral-caudal patterning of the progenitor cells. The fourth cell culture medium is then removed about 252 hours to about 276 hours after the original plating (i.e. about 11 days after original plating). At this time, the cells may be replated on a second laminin-coated substrate, and the fifth cell culture medium is applied. The cells are cultured in the fifth cell culture medium until about 324 hours to about 396 hours after the original plating (i.e. about day 14-16). The fifth cell culture medium may be renewed about 324 hours to about 348 hours after the original plating as well.

After about 14-16 days, the identity of the cells of these processes using the first through fifth cell culture mediums can be verified by expression of regional markers including FOXG1, OTX2, LMX1A, FOXA2, and HOXA2. After about 16 days to about 25 days, the neural cells are ready for cryopreservation or transplantation. If the cells are being used for longer-term studies that need mature neuronal phenotypes, they can be cultured in the sixth cell culture medium. The resulting neural cells are obtained in a large quantity.

The cell culture media of FIG. 2 and FIG. 3 can be compared to each other. The primary cell culture medium of FIG. 2 is similar to the second cell culture medium of FIG. 3. The secondary cell culture medium of FIG. 2 is similar to the fourth cell culture medium of FIG. 3. The quaternary cell culture medium of FIG. 2 (B27M) is similar to the fifth cell culture medium of FIG. 3 (NDM).

The following examples are for purposes of further illustrating the present disclosure. The examples are merely illustrative and are not intended to limit devices made in accordance with the disclosure to the materials, conditions, or process parameters set forth therein.

EXAMPLES

Coating Plates with Laminin-111

Prior to initiating differentiation, about 1 µg/cm² Laminin-111 in PBS and $Ca^{2+}/Mg^{2+}$ (total volume 300 µL) was coated onto a 24 well plate. For a few wells, laminin-111 and PBS were mixed directly into the wells. The plate was shaken to ensure homogenous coating. The plate was then covered with parafilm and left at 4° C. for about 1 to about 7 days before use.

Dilution of CHIR99021

10 mM CHIR99021 stock in DMSO was prepared. The stock was distributed between aliquots (5-10 µL per vial) and stored at −20° C. The aliquots can be thawed up to three times before discarding.

For use in culturing, CHIR99021 was diluted 1:100 in N2M to yield a 100 µM solution prior to adding to the cell culture medium.

Example 1

Materials and Methods

Neural induction medium (NIM), Y-27632 (10 µM), SB431542 (10 µM) and noggin (100 ng/mL) were combined to create a differentiation medium. Approximately 250 µL of medium was needed per cm² of differentiation. For patterning to ventral mesencephalic fates, 0.6 to 1.0 µM CHIR99021 and 200 ng/mL Shh-C24II was added to the medium.

Colonies appeared pluripotent and any differentiated colonies were removed from the culture before initiating differentiation. STEMMACS® iPSBrew medium was aspirated and cells washed once in PBS. EDTA (0.5 mM) was added to the cells and the cells incubated at room temperature for about 7 minutes. The plate was rocked occasionally to ensure the cells were submerged in EDTA.

10 mL wash medium (DMEM/F12 with 0.1% albumin or other medium similar to growth medium) was prepared in a 15 mL tube. EDTA was removed and 1 mL wash medium was transferred to the plate.

Colonies were immediately pipetted off the dish with a pipette and triturated to yield homogenous sizes while avoiding dissociation to single cells. The colonies were then transferred to the 15 mL tube with the wash medium. The cell suspension was mixed and 1 mL suspension was transferred to a 1.5 mL tube for counting. The tube was spun at 400×g for 5 minutes.

Medium from the 1.5 mL tube was aspirated and cells resuspended in 100 µL accutase. The cells were left in an incubator for 7 minutes to yield a single cell suspension. 900 µL wash medium was added to the 1.5 mL tube and cells dissociated with the pipette. Cells were then counted to estimate the total number of cells in suspension. Approximately 10,000 cells/cm² were required to initiate differentiation and transferred from suspension to a new tube before being spun down at 400×g for 5 minutes.

The wash medium was aspirated and re-suspended in a mixed differentiation medium of NIM, Y-27632 (10 µM), SB431542 (10 µM), noggin (100 ng/ml), CHIR99021 (0.7 µM) and SHH-C24II (200 ng/ml) to yield a cell suspension of 50,000 cells/mL. Laminin-111 was aspirated from the coated plate and the cell suspension seeded onto the coated plate with 10,000 cells/cm² (approximately 250 µL medium per cm²). The plate was thoroughly shaken and swirled to yield homogenous cell plating.

After about 48 hours (Day 2), the medium was changed to new neural induction medium (NIM) with SB431542 (10 µM) and noggin (100 ng/mL). For patterning to ventral mesencephalic fates, 0.6 to 1.0 µM CHIR99021 and 200 ng/mL SHH-C24II were added to the medium. The same volume of differentiation medium was used as the volume used to initiate differentiation.

After about 48 hours (i.e., about 96 hours from plating, Day 4), the medium was changed to neural proliferation medium (NPM) with SB431542 (10 µM) and noggin (100 ng/mL). For patterning to ventral mesencephalic fates, 0.6 to 1.0 µM CHIR99021 and 200 ng/mL Shh-C24II were added to the medium. Approximately 350 µL medium was added per cm².

After about 72 hours (i.e., about 168 hours from plating, Day 7), the medium was refreshed with NPM with SB431542 (10 µM) and noggin (100 ng/mL). For patterning to ventral mesencephalic fates, 0.6 to 1.0 µM CHIR99021 and 200 ng/mL Shh-C24II were added to the medium. Approximately 350 µL medium was added per cm².

After about 48 hours (i.e., about 216 hours from plating, Day 9), the medium was changed to NPM with fibroblast growth factor (FGF8b) (100 ng/mL). Approximately 500 µL medium was added per cm².

After about 48 hours (i.e., about 264 hours from plating, Day 11), the cells were replated onto a new 12 well laminin-111 coated plate. Cells were washed twice with PBS and shaken in the plate to remove all dead and floating cells. Approximately 300 µL accutase was added to each well. Cells were left in the incubator for 10 minutes and rocked occasionally to ensure that the cells were submerged in accutase.

A 15 mL tube was prepared with 10 mL NPM. After 10 minutes, the cells were dissociated with a 1 mL pipette to yield a single cell suspension and transferred to the 15 mL tube containing NPM. Cells were spun down at 400×g for 5 minutes. The medium was then aspirated and the cell pellet transferred and resuspended in 1 mL NPM in a 1.5 mL tube. 10 µL cell suspension was removed for counting. The suspension was diluted 1:10-1:50. While counting, cells were spun down at 400×g for 5 minutes.

The medium was aspirated and cells resuspended to a density of 1.7 million cells/mL in B27 medium (B27M), brain derived neurotrophic factor (BDNF) (20 ng/mL), ascorbic acid (AA) (0.2 mM), glial cell line-derived neurotrophic factor (GDNF) (10 ng/mL) and FGF8b (100 ng/mL). Laminin-111 was aspirated from the coated plates and cells seeded onto the plate at a density of 800,000 cells/cm². The plate was thoroughly shaken and swirled to yield homogenous plating of the cells before incubation.

After 72 hours (i.e., about 336 hours after plating, Day 14), medium on the cells was refreshed with B27M, BDNF (20 ng/mL), AA (0.2 mM), GDNF (10 ng/mL), and FGF8b (100 ng/mL). Approximately 500 µL medium was added per cm².

After 48 hours (i.e., about 384 hours after plating, Day 16), the cells were ready for cryopreservation and/or transplantation.

Validation of Progenitor Cell Phenotype

Parallel plates of cells were kept in B27M with BDNF, ascorbic acid, and FGF8b until day 14 (i.e. 336 hours after plating) and then harvested for RNA analysis or fixed for immunocytochemistry. On day 14, the regional identities of the cells were clearly identified by their expressions of regional markers such as FOXG1, OTX2, LMX1A, FOXA2, and HOXA2.

Example 2

Materials and Methods

The same materials and protocol disclosed in Example 1 are used for 24 well plates with the following alterations:

Plates were coated with laminin-111 (1 μg/cm$^2$) in PBS and Ca$^{2+}$/Mg$^{2+}$ (700 μL/cm$^2$). For seeding the cell suspension onto the laminin-111 coated plates, approximately 250 μL was required per cm$^2$ (500 μL/well). To initiate differentiation, for 6 wells of a 24 well plate, 120,000 cells in total were needed.

At the 96 hour and 168 hour marks after plating, approximately 600 μL medium was added to each well. At the 216 hour mark after plating, approximately 700 μL medium was added to each well.

Some cell lines required the addition of 10 μM Y-27632 to the medium to survive replating. During replating, approximately 150 μL accutase was added to each well. At the 336 hour mark, approximately 700 μL medium was added per well.

Example 3

Preparation of Cells for Transplantation (Day 16-25)

The same materials and protocol disclosed in Examples 1 and 2 are used.

Cells were maintained in B27M, BAG (BDNF+AA+GDNF), and FGF8b until the day of transplantation without any further manipulations. Medium was refreshed every 2-3 days. Cells were most suitable for transplantation on day 16 but could be transplanted up until day 26. Cells for transplantation did not receive DAPT or db-cAMP in the medium, as this would result in premature neuronal maturation and increased cell death upon dissociation.

Example 4

Long-Term Terminal Neuronal Maturation

The same materials and protocol disclosed in Examples 1 and 2 are used.

Cells for long-term studies of mature neuronal phenotype were replated again between days 16 and 25 to avoid too high densities of cultures and detachment of cells. Cells were kept in B27M and BAG (without db-cAMP and DAPT) until the day of replating. Replating was performed using the same procedure as used on Day 11 (i.e., 264 hours after first plating), and cells were kept in B27M, BDNF (20 ng/mL), GDNF (10 ng/mL), ascorbic acid (0.2 mM), db-cAMP (500 μM), and DAPT (1 μM) after replating.

Replating at later timepoints should be avoided due to stress on mature neuronal cells. At late stages of differentiation, neurons may begin to detach from the plate. This can be attenuated by adding laminin and fibronectin (FN) to the cell culture medium. Mature dopaminergic phenotypes only start to appear from Day 45 and onwards.

Example 5

Over the past 6 years, over 500 rats were intracerebrally transplanted with 31 different batches of hES cell-derived mesDA progenitors at various different research sites. An overview of the graft experiment plan is reflected in Tables 2-3 below. For graft site: Str.=striatum, SN=substantia nigra. For rat host strain, SD=Sprague-Dawley, LH=Listerhooded, At=Athymic Crl:NIH-Foxn1rnu. For immunosuppression, Ciclo=daily intraperitoneal injections of ciclosporin (10 mg/kg), starting the day before transplantation.

TABLE 2

| Batch # | Graft Survival | Animals ($n_{analysed}/n_{grafted}$) | Graft Site | Rat host strain | Immuno-suppression | # Grafted Cells | Avg. Yield (TH+ cells/ 100,000 grafted) |
|---|---|---|---|---|---|---|---|
| 1 | 6 weeks | 7/7 | Str. | SD | Ciclo | 3 × 10$^5$ | 3711 |
| 2 | 6 weeks | 8/8 | Str. | SD | Ciclo | 3 × 10$^5$ | 4616 |
| 3 | 6 weeks | 7/7 | Str. | SD | Ciclo | 3 × 10$^5$ | 8660 |
| 4 | 6 weeks | 7/7 | Str. | SD | Ciclo | 3 × 10$^5$ | 5597 |
| 5 | 8 weeks | 7/10 | Str. | SD | Ciclo | 3 × 10$^5$ | 19876 |
| 6 | 24 weeks | 6/6 | Str. | AT | — | 3 × 10$^5$ | 9260 |
| 7 | 16 weeks | 14/15 | Str. | LH | Ciclo | 3 × 10$^5$ | 273 |
| 8 | 24 weeks | 4/9 | SN | AT | — | 1 × 10$^5$ | 38 |
| 11 | 24 weeks | 9/16 | Str. | LH | Ciclo | 3 × 10$^5$ | 266 |
| 12 | 24 weeks | 8/8 | SN | AT | — | 1 × 10$^5$ | 4007 |
| 13 | A: 6 weeks | 3/4 | Str. | SD | Ciclo | 2 × 10$^5$ | 212 |
|  | B: 6 weeks | 3/4 | Str. | SD | Ciclo | 2 × 10$^5$ | 176 |
| 14 | 6 weeks | 5/6 | Str. | SD | Ciclo | 2 × 10$^5$ | 170 |
| 16 | 6 weeks | 4/4 | Str. | SD | Ciclo | 1.5 × 10$^5$ | 1052 |
| 17 | 24 weeks | 10/10 | Str. | AT | — | 3 × 10$^5$ | 2198 |
| 18 | A: 4 weeks | 4/4 | Str. | SD | Ciclo | 3 × 10$^5$ | 581 |
|  | B: 16 weeks | 5/8 | Str. | SD | Ciclo | 3 × 10$^5$ | 1011 |
| 19 | A: 4 weeks | 3/4 | Str. | SD | Ciclo | 3 × 10$^5$ | 36 |
|  | B: 16 weeks | 7/8 | Str. | SD | Ciclo | 3 × 10$^5$ | 261 |

TABLE 2-continued

| Batch # | Graft Survival | Animals ($n_{analysed}/n_{grafted}$) | Graft Site | Rat host strain | Immuno-suppression | # Grafted Cells | Avg. Yield (TH+ cells/ 100,000 grafted) |
|---|---|---|---|---|---|---|---|
| 20 | 6 weeks | 4/4 | Str. | SD | Ciclo | $1.5 \times 10^5$ | 755 |
| 21 | 6 weeks | 4/4 | Str. | SD | Ciclo | $1.5 \times 10^5$ | 13 |
| 22 | A: 18 weeks | 4/4 | Str. | SD | Ciclo | $2 \times 10^5$ | 6868 |
|  | B: 24 weeks | 6/6 | Str. | AT | — | $3 \times 10^5$ | 5822 |
| 23 | A: 18 weeks | 3/4 | Str. | SD | Ciclo | $2 \times 10^5$ | 4141 |
|  | B: 24 weeks | 5/5 | Str. | AT | — | $3 \times 10^5$ | 3549 |
| 24 | 6 weeks | 2/2 | Str. | SD | Ciclo | $4 \times 10^5$ | 9 |
| 25 | 18 weeks | 4/4 | Str. | SD | Ciclo | $4 \times 10^5$ | 7.5 |
| 26 | 16 weeks | 5/7 | Str. | SD | Ciclo | $2.4 \times 10^5$ | 963 |
| 27 | 16 weeks | 5/8 | Str. | SD | Ciclo | $2.4 \times 10^5$ | 3970 |
| 28 | 16 weeks | 3/7 | Str. | SD | Ciclo | $2.4 \times 10^5$ | 1117 |
| 29 | 18 weeks | 5/5 | Str. | SD | Ciclo | $1.5 \times 10^5$ | 7054 |
| 30 | 18 weeks | 4/4 | SN | SD | Ciclo | $0.75 \times 10^5$ | 4484 |
| 31 | 20 weeks | 9/9 | Str. | LH | Ciclo | $3.4 \times 10^5$ | 5200 |

TABLE 3

| Batch # | Avg. Vol./ 100,000 (mm³) | Avg. TH+/ Vol. (mm³) | Included in DeSeq2 + PCA | Included in FIG. 7D and 7E | Included in FIG. 6G |
|---|---|---|---|---|---|
| 1 | 1008 | 3790 | DA-high |  |  |
| 2 | 1141 | 3972 | DA-high |  |  |
| 3 | 2394 | 3579 | DA-high |  |  |
| 4 | 1366 | 4001 | DA-high |  |  |
| 5 | 4413 | 4479 |  |  |  |
| 6 | 2897 | 3335 | DA-high |  |  |
| 7 | 0074 | 2861 | DA-low |  |  |
| 8 | ND | ND |  | X | X |
| 11 | 0118 | 2425 | DA-low |  |  |
| 12 | ND | ND |  |  |  |
| 13 | 0074 | 2485 | DA-low |  |  |
|  | 0054 | 1583 | DA-low |  |  |
| 14 | 0049 | 4080 | DA-low |  |  |
| 16 | 1606 | 658 |  |  | X |
| 17 | 0537 | 7387 | DA-high | X |  |
| 18 | 0085 | 5936 | DA-low | X | X |
|  | 0144 | 5894 | DA-low | X |  |
| 19 | 0028 | 923 | DA-low | X | X |
|  | 0057 | 4772 | DA-low | X |  |
| 20 | 0294 | 3791 |  |  | X |
| 21 | 0026 | 527 |  |  |  |
| 22 | 1380 | 3573 |  | X | X |
|  | 1820 | 3536 |  | X | X |
| 23 | 0872 | 4754 | DA-high |  | X |
|  | 0881 | 3999 | DA-high |  |  |
| 24 | 0043 | 345 | DA-low |  | X |
| 25 | 0016 | 580 | DA-low |  | X |
| 26 | 0856 | 1822 |  |  | X |
| 27 | 0828 | 4461 | DA-high |  | X |
| 28 | 0208 | 4869 |  |  | X |
| 29 | 1640 | 4509 | DA-high | X | X |
| 30 | 1532 | 2911 | DA-high | X | X |
| 31 | 1430 | 3787 |  |  | X |

Figure 4A:
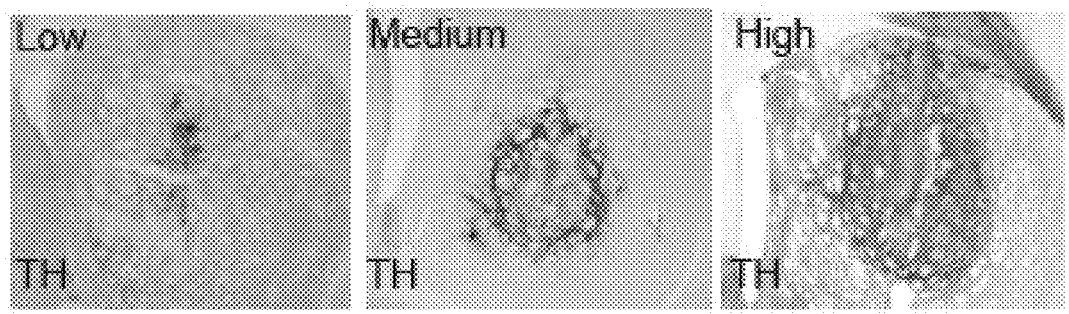
Figure 4B:
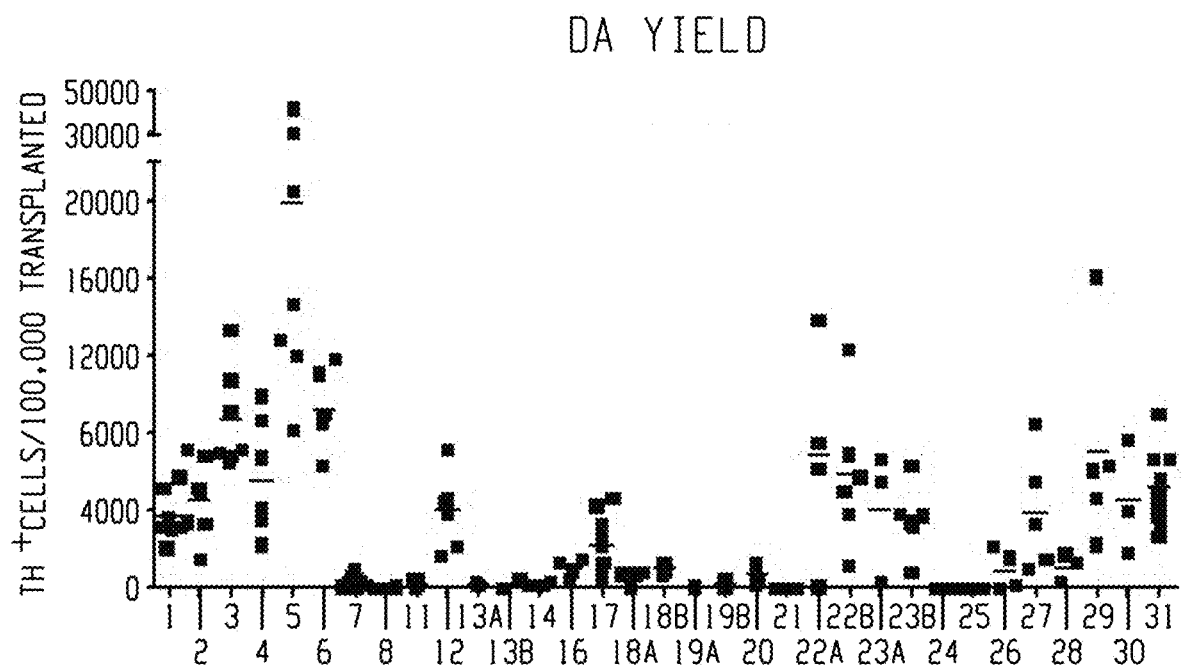
Figure 4C:
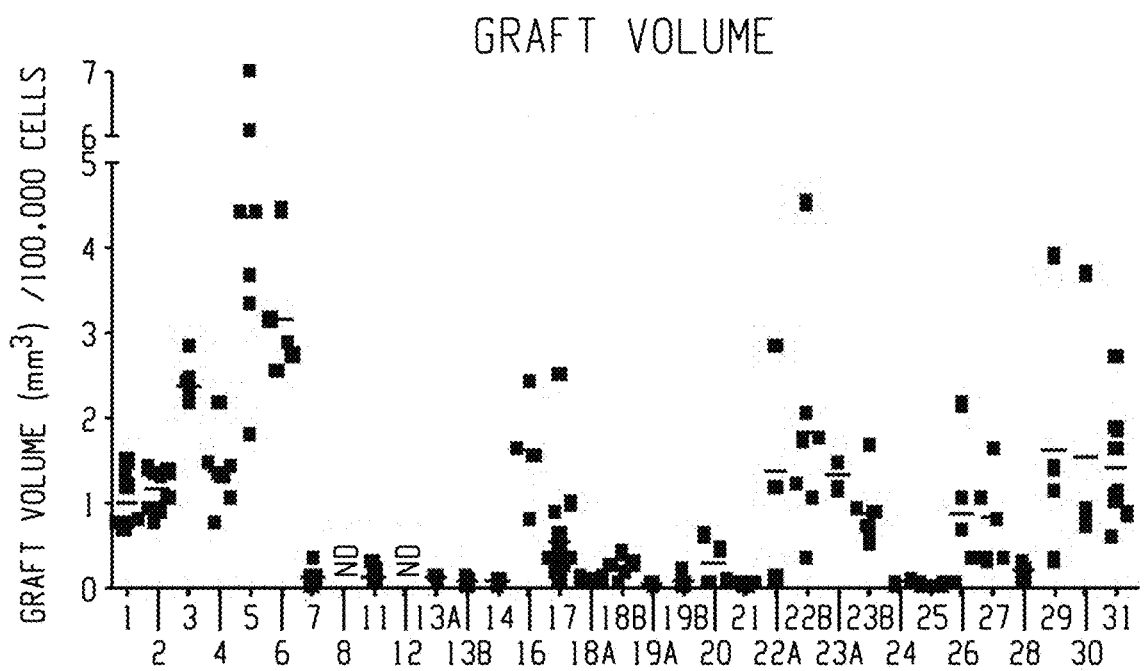
Figure 4D:
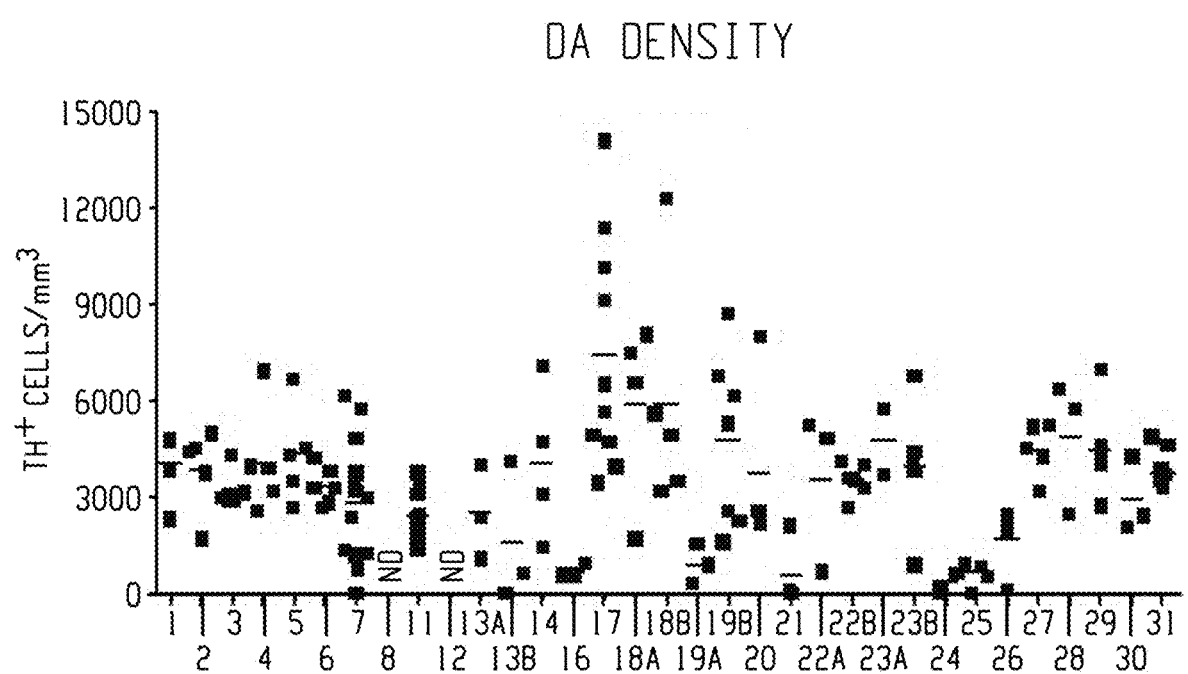
Figure 4E:
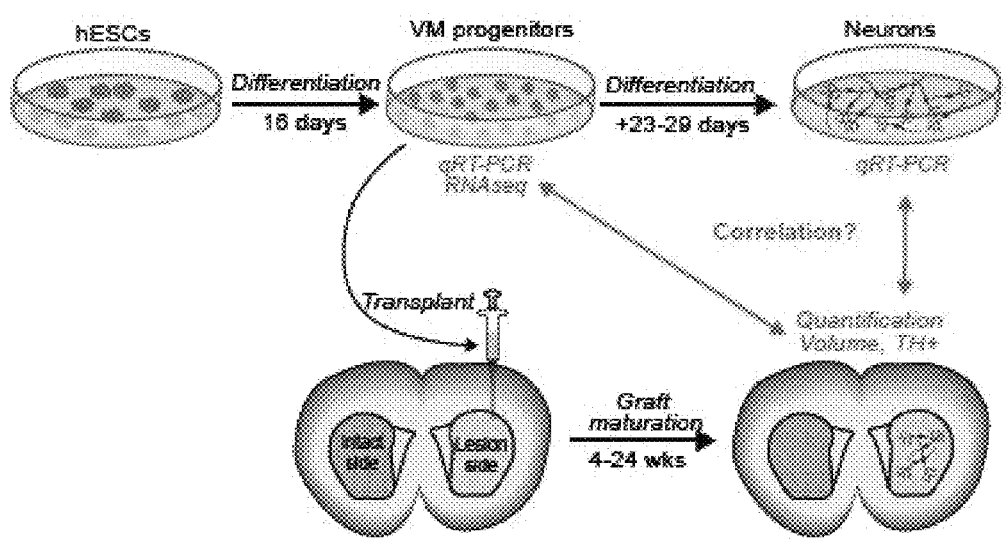

In all experiments, the scheme of which is illustrated in FIG. 4E, hESCs were differentiated for 16 days in vitro, and various different batches of ventral mesencephalic-patterned hESCs were grafted into rats subjected to unilateral dopaminergic lesions with 6-OHDA. FIG. 4A is set of photographs of the grafts after the cells matured in vivo, and the brains were stained with TH. Although all ventral mesencephalon-patterned cell batches were routinely assessed for high expression of ventral mesencephalon markers LMX1A, FOXA2, and OTX2 prior to grating, the in vivo outcome with respect to graft size and number of dopamine neurons varied between experiments.

To determine the level of batch-to-batch variability from these experiments, the total number of TH+ neurons of each animal per 100,000 cells grafted (DA yield) was quantified, which is graphically illustrated in FIG. 4B, and the graft size was based on HuNu+ cell volume (mm³) following immunostaining. The graphical representation of graft volume is seen in FIG. 4C. For all quantifications, values were reported per 100,000 cells grafted. This permitted estimation of DA densities (TH+/mm³) for all grafts, which are represented in FIG. 4D. These quantitative assessments revealed considerable inter-experimental variability.

To determine what degree commonly used mesDA progenitor marks in vitro predicted TH+ content in grafts after maturation in vivo, RNA samples were collected from each individual cell batch enumerated above (all containing high levels of FOXA2/LMX1A co-expressing cells) at the day of transplantation and analyzed. RNA samples from the same cells replated were also analyzed after further in vitro maturation.

FIG. 4F is a set of graphs indicating the mean TH+ cell content in each graft experiment plotted versus gene expression of FOXA2, LMX1A, and CORIN in the transplanted cell population on day 16 (i.e. day of transplantation). Similarly, FIG. 4G is also a set of graphs representing transplanted cell population on day 16, but the graphs indicate the gene expression of TH, NURR1, and AADC. Results from a Spearman correlation (ventral mesencephalon cells only) are given as R and p-values in each graph, and the tendencies of correlation are shown by linear regression lines.

It was found that expression of commonly used mesDA markers FOXA2, LMX1A, and CORIN was required for dopaminergic differentiation of the grafts. However, FOXA2 and LMX1A expression levels at the time-point of transplantation did not correlate significantly with DA yield in the grafts, suggesting that within the FOXA2/LMX1A co-expressing cells, additional markers are needed to predict the in vivo outcome.

FIGS. 4F and 4G represent an assessment of whether extended in vitro maturation of the progenitors into neurons reflected their corresponding in vivo maturation in the grafts. In further experiments where the cells used for grafting had also been subjected to parallel terminal differentiation in vitro for 39-45 days (instead of only 16 days), it was found that the expression levels of DA markers TH, NURR1, and AADC did not show any statistically significant correlation to DA yield after transplantation.

Example 6

To enable an unbiased search for potential markers which correlate positively with DA yield after transplantation (i.e. successful graft outcome), global gene expression profiling was performed of cell samples collected at the day of transplantation using RNA sequencing.

For unbiased gene expression analysis, graft experiments were divided into DA-high and DA-low groups based on the total number of TH+ cells in the grafts. A graphical comparison of the TH+ content between batches is shown in FIG. 5A. Dopaminergic function of the grafts was assessed in grafts with longterm maturation (i.e. longer than 16 weeks) through amphetamine induced rotation or PET imaging. A "−" symbol indicates a lack of functional recovery, a "+" symbol indicates functional recovery, and "ND" indicates "not determined.

Importantly, all longterm grafts with lack of functional recovery were located in the DA-low group, whereas the DA-high group contained cells with therapeutic potential able to mediate functional recovery.

To see if the DA-high and DA-low cell batches could be identified by distinct gene expression profiles, an unbiased principal component analysis (PCA) was performed on all the selected day 16 RNA sequencing samples. As shown in FIG. 5B, a clustering of the DA-high samples was observed positive PC1 axis, which contained genes such as FGF8, PAX5, EN2, and CNPY1, all of which have been shown to be important for midbrain-hindbrain boundary (MHB) formation.

Figure 5E:
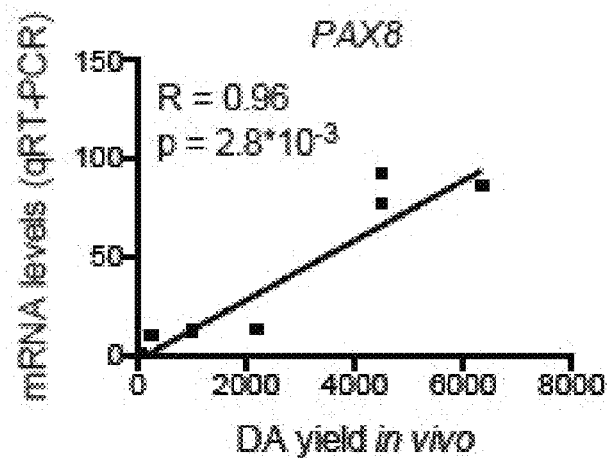

As there were clearly distinct expression profiles between the two groups, a Deseq2 analysis was conducted to identify all differentially expressed genes between the DA-high and DA-low samples. FIG. 5I is a graphical analysis of predictive markers following the Deseq2 analysis of RNA sequencing data from DA-high and DA-low cell samples. Markers were plotted based on log 2 fold change compared to mean of normalized counts. From the top 12 ranked genes appearing from this analysis, again a high representation was found of genes expressed in the caudal ventral mesencephalon and MHB regions to be positively associated with DA yield in vivo, i.e. PAX5, FGF8, SPRY1, EN1, EN2, SP5, ETV4, CNPY1, TLE4, and ETV5. These expression profiles are reflected in FIG. 5C. These 12 genes are those with the highest fold change and with a p-value of <0.001.

To assess the predictive value of these selected markers, a direct Spearman correlation analysis was conducted between graft outcomes (i.e. TH+ content) to the RNA expression levels of selected genes from the PCA and Deseq2 analyses. FIGS. 5D-5E specifically show the results from the Spearman correlation analysis for EN1 and PAX8. Results from the Spearman correlation analysis were given as R and p-values, and correlations were visualized with linear regression lines. To validate the RNA sequencing dataset, a subset of gene correlations was assessed using qRT-PCR, including 4 additional graft experiments, which are represented as FIG. 5E specifically.

Figure 5F:
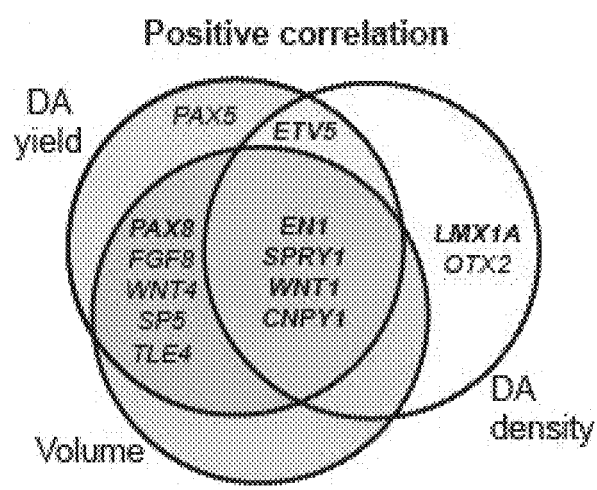

A summary of the RNA sequencing correlation analysis between TH+ content, graft volume, and DA density and RNA levels of MHB genes and common ventral mesencephalon markers is shown in FIG. 5F. The schematic only shows positive correlations defined by the Spearman correlation analysis with p<0.05. Genes verified by qRT-PCR are shown in bold.

These correlations were compared to the correlations of commonly used ventral mesencephalon markers (i.e., LMX1A, LMX1B, FOXA2, FOXP2, CORIN, and OTX2).

Figure 5G:
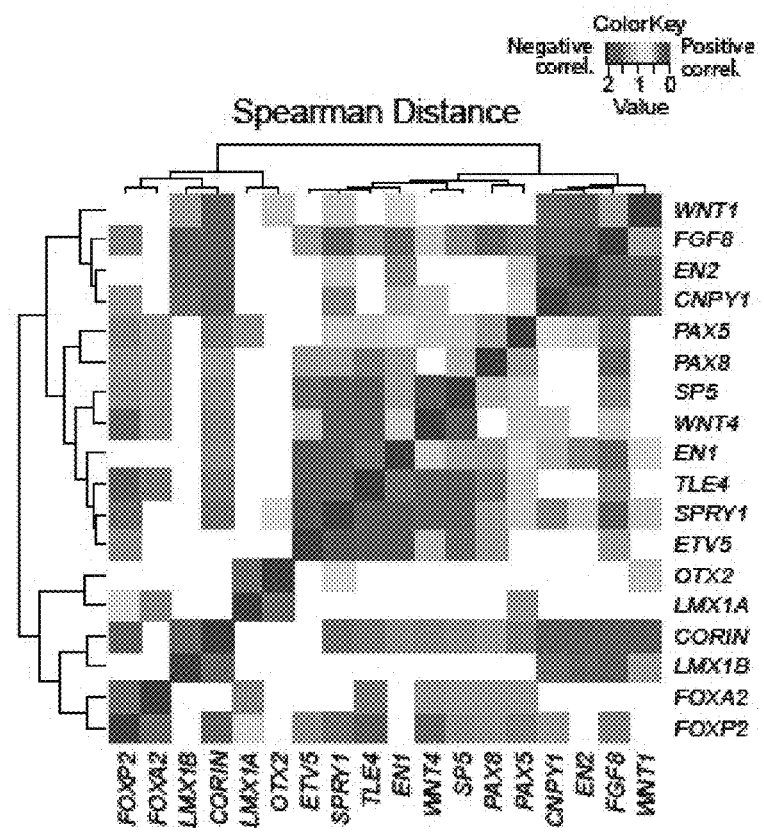

The analyses showed that most of the caudal ventral mesencephalon markers identified by DeSeq2 showed positive correlation with graft size and total TH content of the grafts, as shown in FIG. 5G. FIG. 5G in particular is a graphical representation of a Spearman distance analysis of RNA levels in cell batches, showing co-regulation of MHB genes. Markers EN1, SPRY1, WNT1, ETV5, and CNPY1 correlated positively with DA density (TH+/mm$^3$). These contrasted to the broader and more widely expressed ventral mesencephalon markers FOXA2, LMX1A, CORIN, FOXP1, and FOXP2, which by several analyses showed negative correlations to both graft size and total DA yield, indicating they may be uncoupled or negatively coupled to the MHB genes cluster. LMX1A and OTX2 showed positive correlations only to DA density but not to DA yield of the grafts.

Figure 5H:
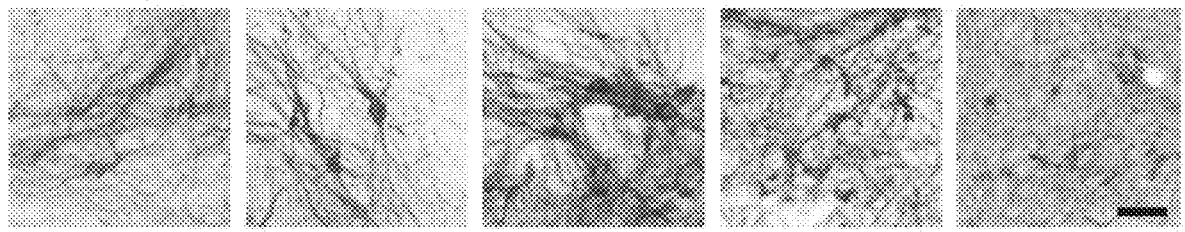
Figure 5I:
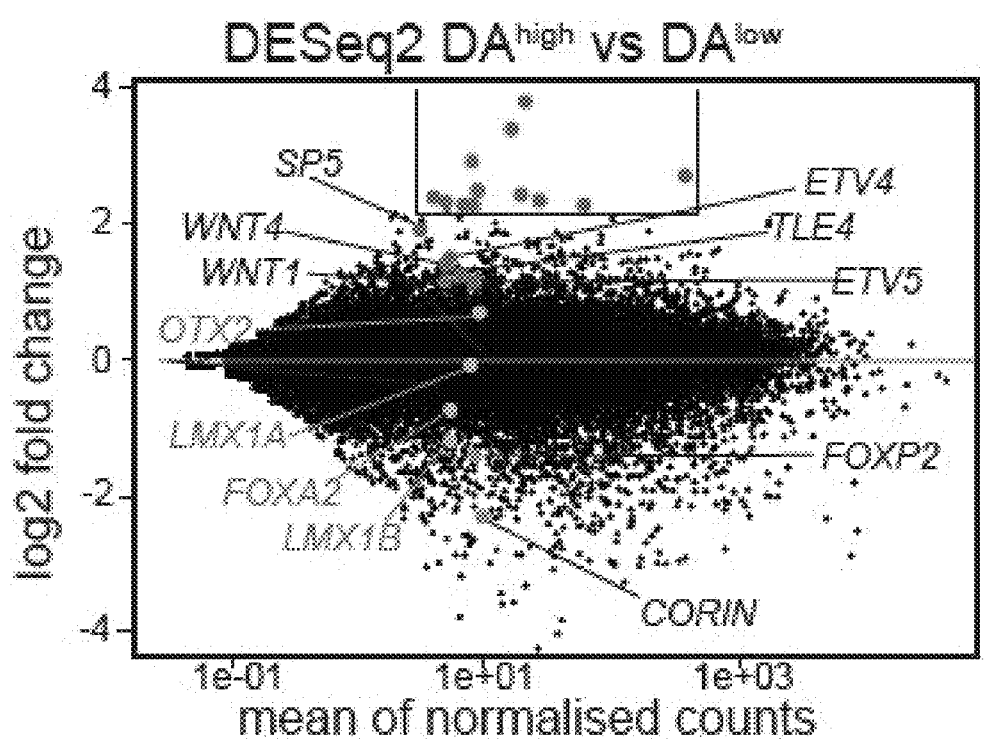

To investigate whether the genes identified in the RNA sequencing analysis formed part of a co-regulated gene network, a Spearman correlation analysis was performed of the expression values for each candidate gene towards others in 29 batches of ventral mesencephalon-patterned cells. As seen in FIG. 5G, all of the MHB genes associated with high DA yield showed a pattern of co-regulation. In particular, the MHB markers SPRY1 and ETV4/5 and the caudal ventral mesencephalon markers EN1 and CNPY1 clustered in the analysis, suggesting a strong co-regulation between the genes. However, LMX1A and OTX2 showed little or no positive co-regulation with these genes. CORIN, LMX1B, FOXA2, and FOXP2 were negatively correlated with several of the caudal genes, indicating that these commonly used markers are not specifically associated with a caudal ventral mesencephalon phenotype and that they may be expressed at higher levels in the more rostral domains of the ventral mesencephalon. Other ventral mesencephalon markers reported to be involved in mesDA neurogenesis, namely MSX1, SOX6, and PBX1, did not show any correlations to DA density of the grafts when analyzed in d16 ventral mesencephalon-patterned progenitors. FIG. 5H is a set of five representative images of TH+ neurons from different cell batches with high expression of predictive markers, revealing the mature morphology of the grafted cells.

Example 7

Figure 6A:
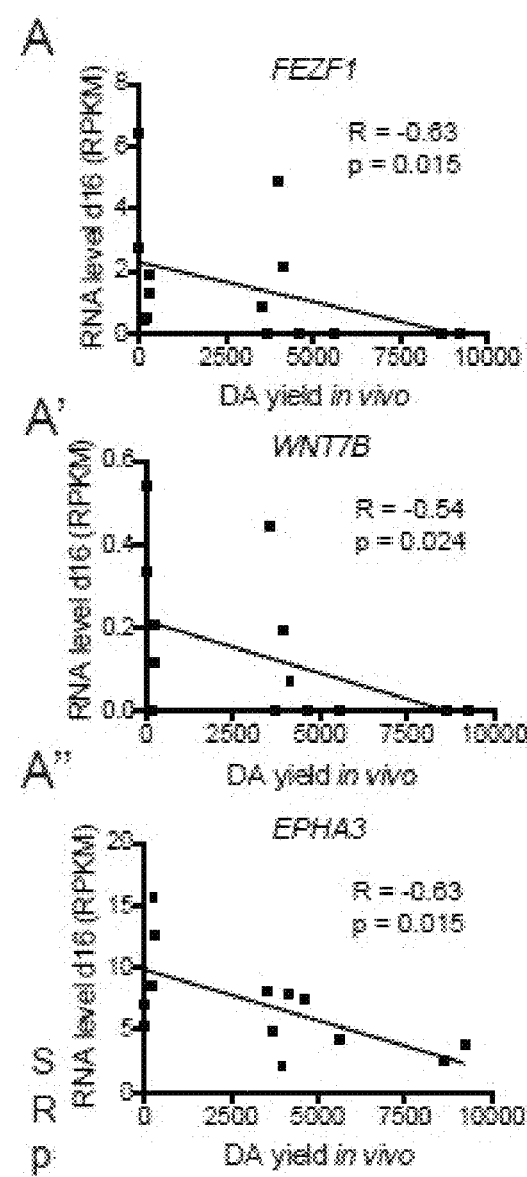
FIGS. 6A-6F are a set of images and graphs indicating that ventral mesencephalic-patterned hESC cultures contain cells of diencephalic STN fates.

Using RNA sequencing expression values, a strong negative correlation was found between the diencephalic markers FEZF1, WNT7B, and EPHA3 and DA yield in grafts at day 16, as shown in FIG. 6A. This correlation led to an investigation of whether some batches of ventral mesencephalon-patterned hESCs contained BARHL1$^+$ and PITX2$^+$ STN progenitors were derived from the anterior LMX1A$^+$/FOXA2$^+$ domain.

Figure 6B:
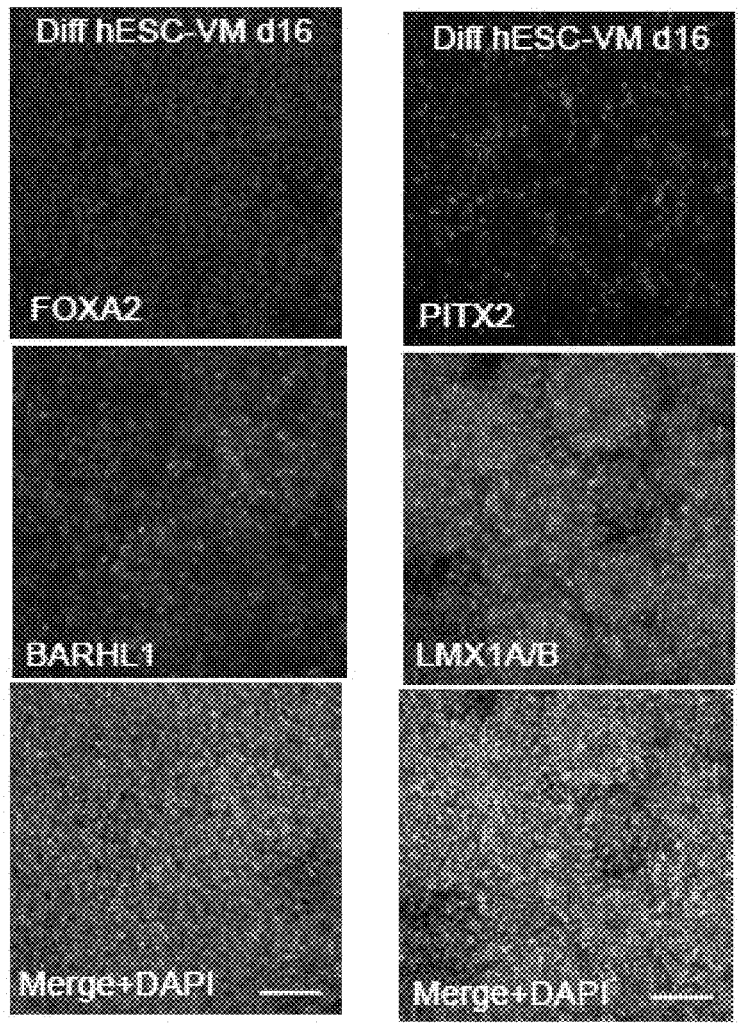

Both BARHL1$^+$ and PITX2$^+$ were detected in the differentiated cell batches on day 16. FIG. 6B is a set of images following immunostaining of ventral mesencephalic-patterned hES cell cultures at day 16, revealing the presence of STN domain fates (i.e. BARHL1$^+$/FOXA2$^+$ and PITX2$^+$/

Figure 6C:
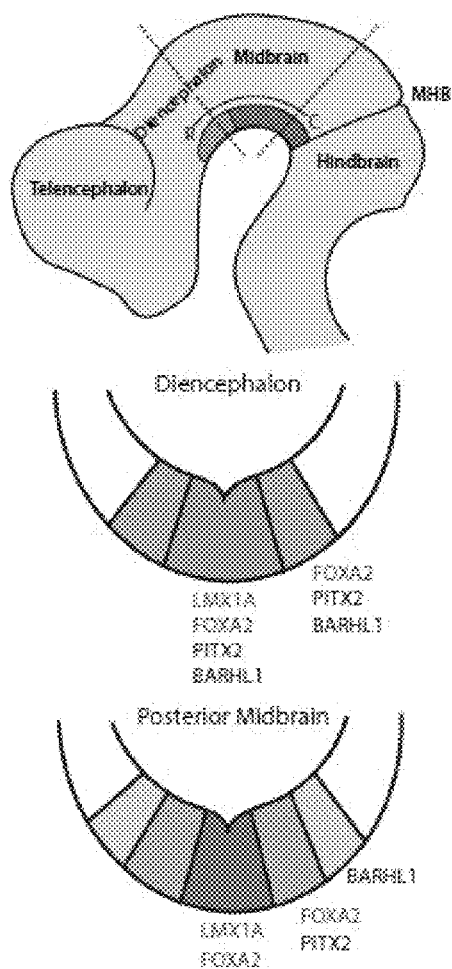

LMX1+ cells). FIG. 6C is a schematic overview of expression domains of PITX2 and BARHL1 in the diencephalic STN region and in lateral midbrain domains. FIG. 6G shows the cell cultures of FIG. 6B at day 42 of differentiation.

As depicted in FIGS. 6B-6C, the BARHL1+ cells could have been either FOXA2+ or FOXA2−, indicating the presence of both diencephalic floorplate cells as well as lateral cell populations in the differentiated progenitor batches. It was further found that FOXA2+/BARHL1+/MAP2+ neurons and PITX2+/LMX1A/B+ cells were present in the terminally differentiated hES cell cultures, indicating the differentiation of these progenitors into STN fates.

Figure 6D:
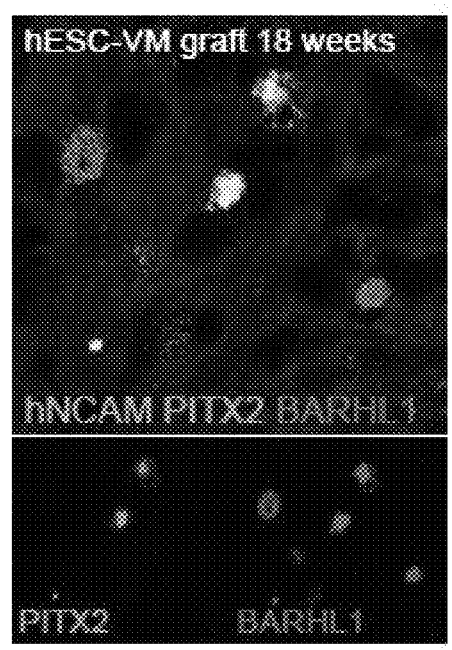
Figure 6E:
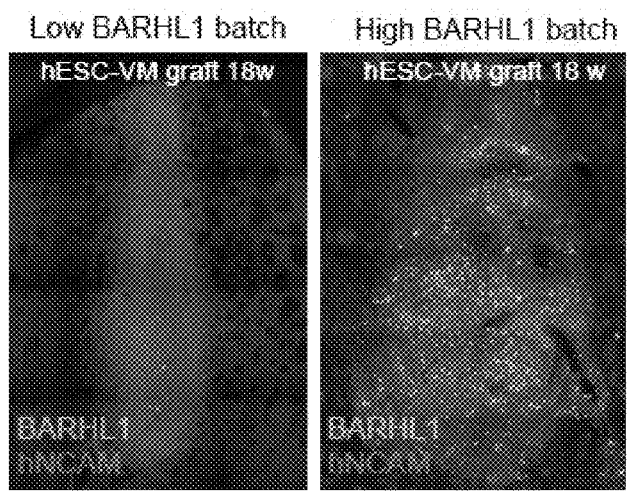

FIG. 6D is a set of images following confocal imaging of 18 week old grafts. In animals grafted with ventral mesencephalon-patterned cells, variable presence of BARHL1+ cells was detected, and these cells would have been either PITX2+ (indicating ventral diencephalic STN fates) or PITX2− (indicating other lateral fates). Example images of BARHL1 cell content in grafts derived from cell batches with low or high BARHL1 RNA levels at the day of transplantation are shown in FIG. 6E.

Figure 6F:
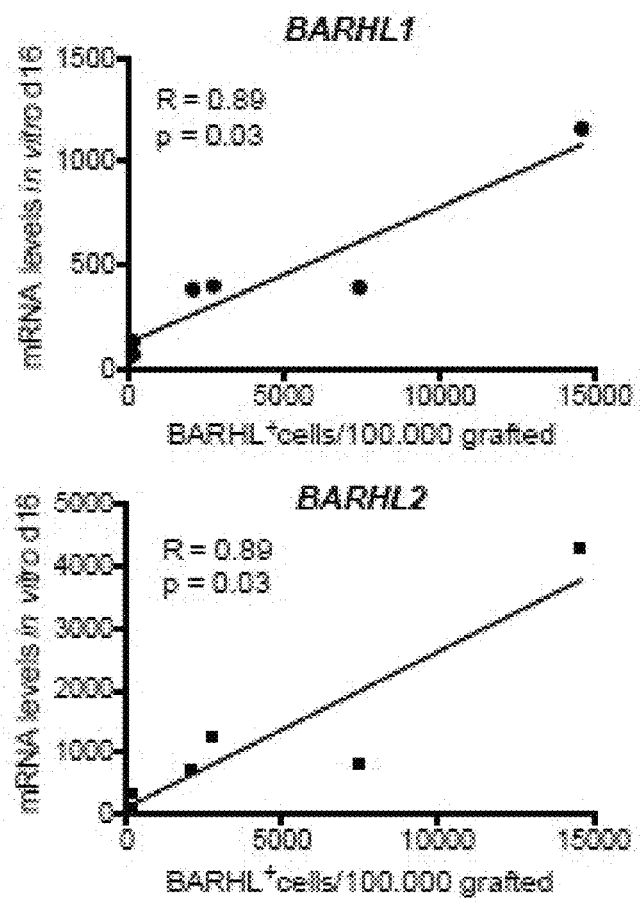
Figure 6G:
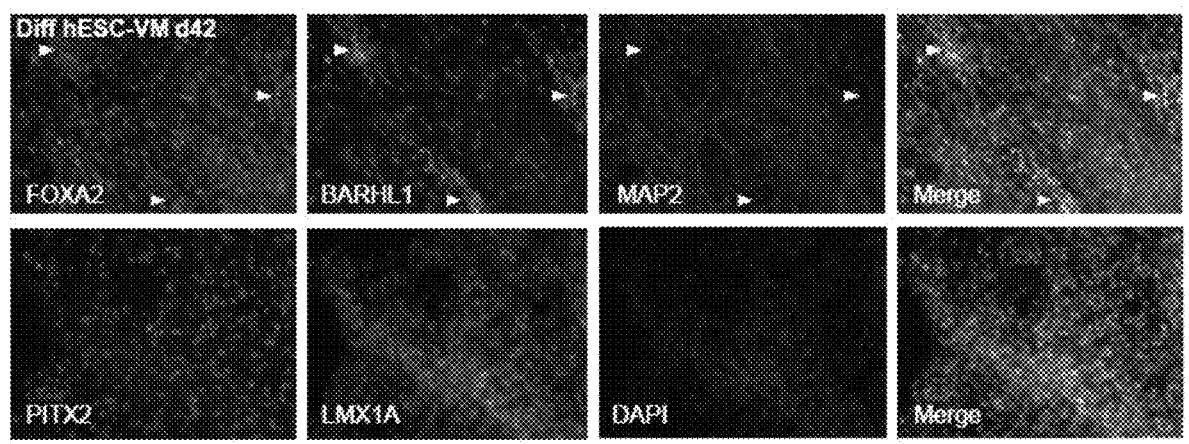
FIG. 6G is a set of eight images of immunostainings of ventral mesencephalic-patterned hESC cultures (day 42, similar to FIG. 6B), showing the terminal in vitro differentiation of cultures with STN fates.

To investigate if these markers could be used to predict the amount of non-dopaminergic lateral and rostro-ventral contaminating cells in the grafts, the numbers of BARHL1 cells were quantified in several of the graft experiments. Correlation analysis showed that the density of BARHL1+ cells in the grafts positively correlated with the expression levels of BARHL1 and BARHL2 in vitro in the differentiated cell batches at the day of transplantation, as shown in FIGS. 6D and 6F. Results from the Spearman correlation analysis are given as R and p-values in each graph, and correlations are visualized with linear regression lines.

These results implied that BARHL1 and BARHL2 in progenitor cultures could be used as markers for identifying and quantifying several commonly occurring contaminating populations in ventral mesencephalon-patterned hESCs both in vitro and in vivo.

Example 8

Given the variable outcome of ventral mesencephalon-patterned hES cell progenitors, it was next investigated if the patterning in differentiation protocol could be optimized toward the caudal dopaminergic domain of the ventral mesencephalon (because markers of this domain correlated with high DA yield in vivo). Cells located in the caudal ventral mesencephalon are in proximity to the MHB, and studies in the mouse and chick models have shown that the development of mesDA progenitors in this region depends on the activity of FGF8, a growth factor that is secreted from the MHB. In addition, high expression of FGF8 was found to correlate to the DA-high group in the gene expression analyses as seen in FIG. 5C above.

Figure 7A:
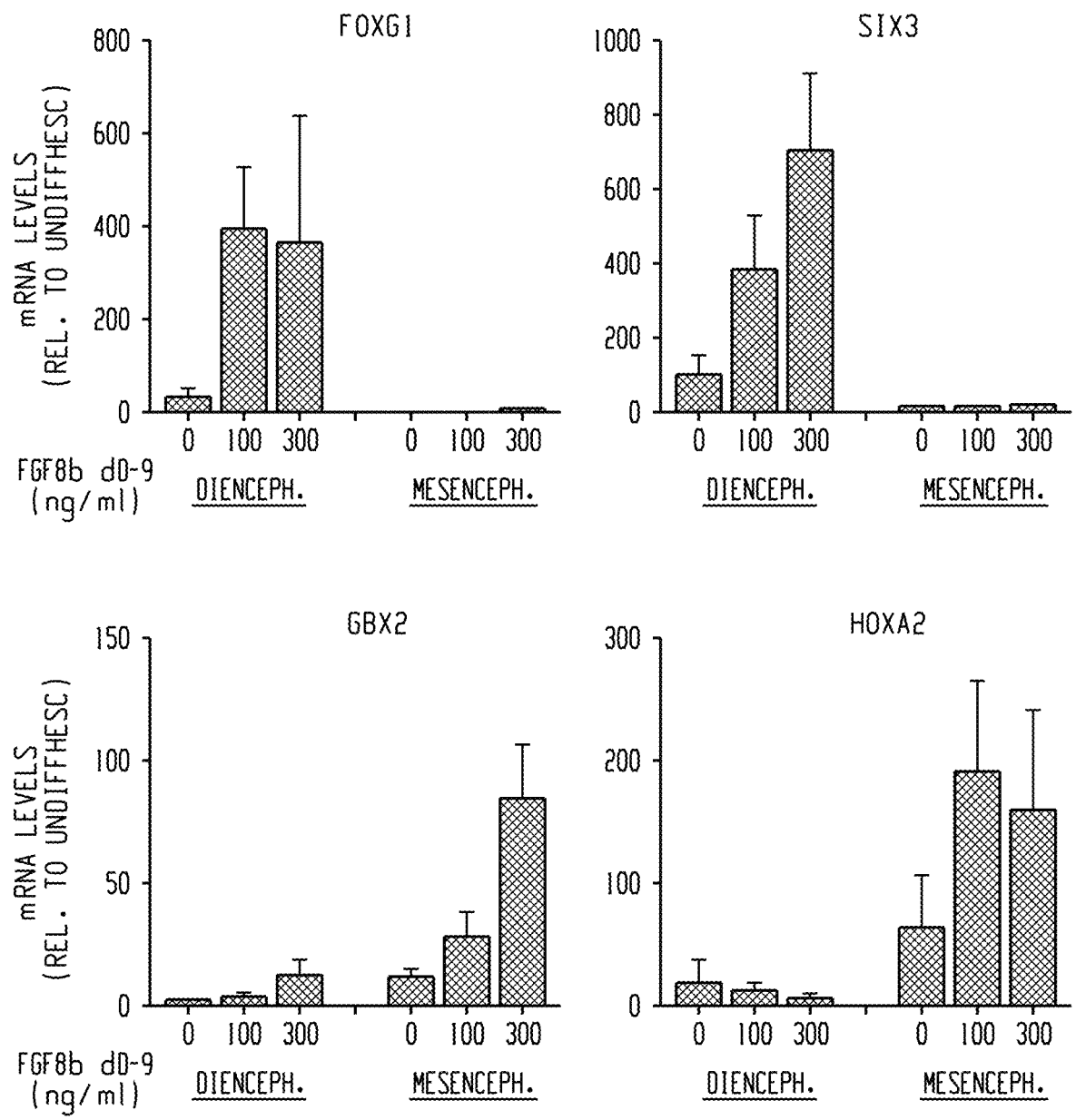
FIGS. 7A-7I are a set of images and graphs indicating that timed delivery of FGF8 to hESCs causes cell fates to switch from diencephalic to caudal ventral mesencephalic progenitors. In vitro studies used data from both H9 and RC17 lines.

FIG. 7A is a set of graphs created following a qRT-PCR analysis at day 10 of differentiating hESCs treated with exogenous FGF8b during ventral mesencephalon patterning from days 0-9. The analysis shows induction of forebrain and hindbrain markers in ventral diencephalic (CHIR=0.4 µM) or ventral mesencephalic (CHIR=0.8 µM) cultures.

Figure 7B:
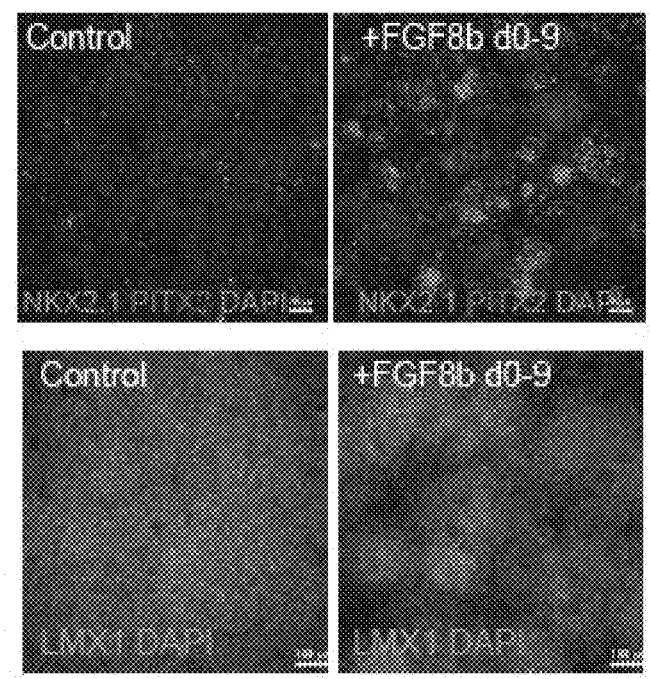

It was found that the addition of FGF8b to the differentiation medium together with SHH and GSK3i to activate canonical WNT signaling during the early phase of neural induction and patterning (day 0-9) induced significant upregulation of forebrain markers FOXG1 and SIX3 in diencephalic-patterned cultures and of hindbrain markers HOXA2 and GBX2 in mesencephalic-patterned cultures. This indicated that early patterning with FGF8b caused contamination of cultures with several non-ventral mesencephalon progenitor fates. FIG. 7B is a set of images following immunostaining at day 16, revealing patches of PITX2+ and NKX2.1+ cells and patches of LMX1A− cells in cultures treated with FGF8b from days 0-9.

Figure 7C:
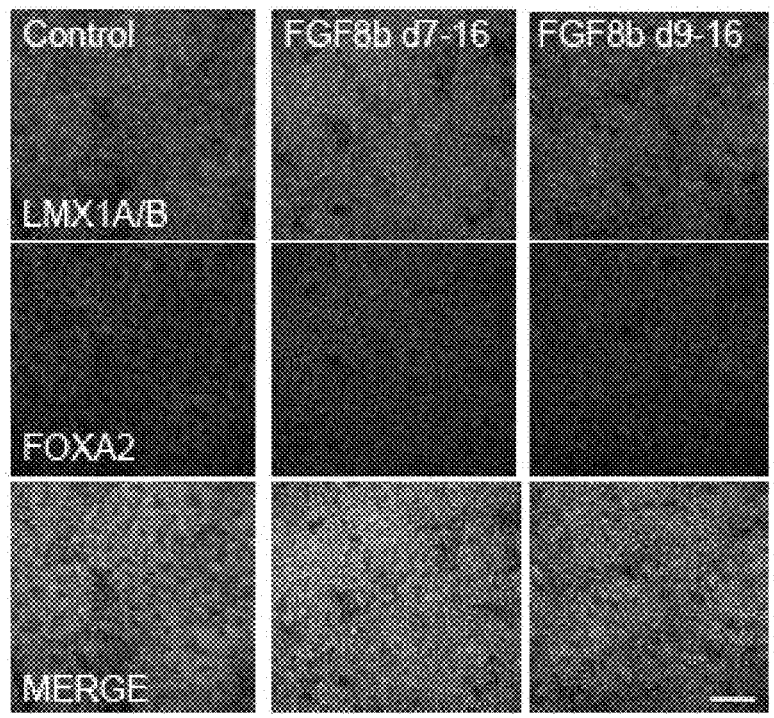

In contrast, the FOXA2+/LMX1A+ phenotype of the cells was maintained, as shown in FIG. 7C, if FGF8b was added to the cells after initial patterning towards ventral mesencephalon was completed (from day 7-16 or 9-16).

Figure 7D:
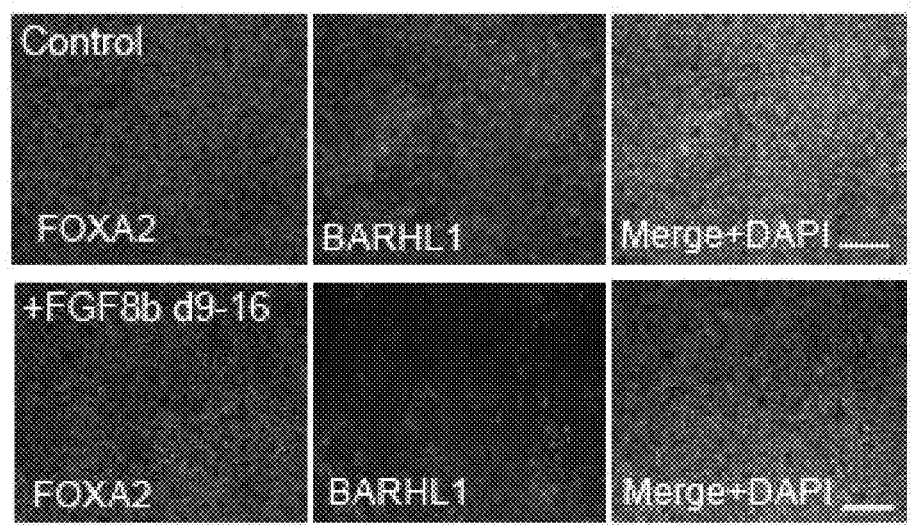
Figure 7E:
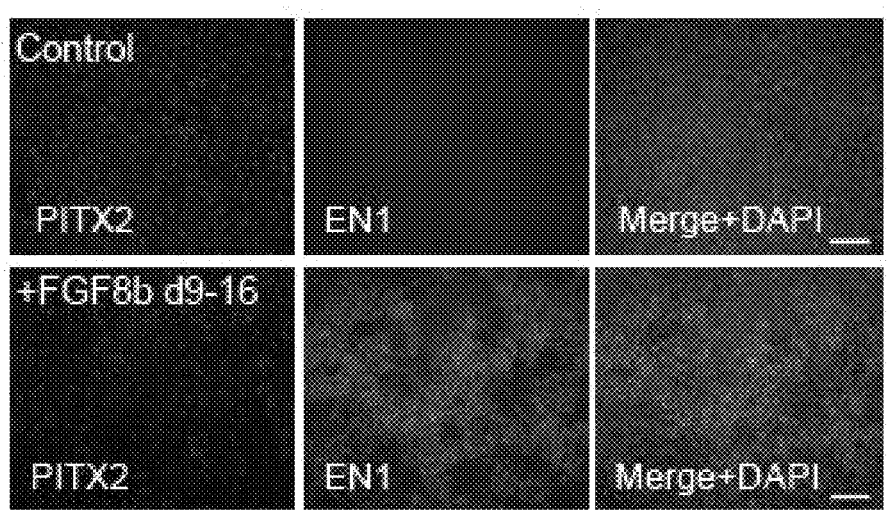
Figure 7F:
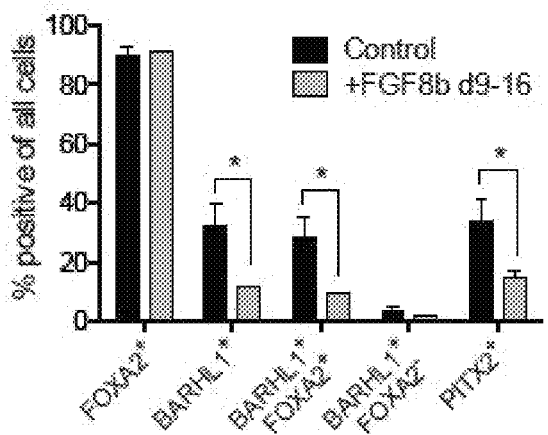
Figure 7G:
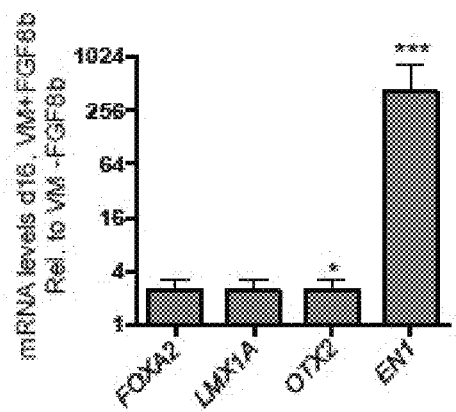

FIGS. 7D-7F correspond to day 16 cultures treated with FGF8b. The addition of 100 ng/mL FGF8b caused caudalisation of the ventral mesencephalon progenitors when the cultures were treated with FGF8b from day 9-16. As shown in the immunostaining images of FIG. 7D-7E, the results of which were quantified in FIG. 7F, BARHL1+ and PITX2+ levels were both decreased. However, whereas control ventral mesencephalon cultures were completely devoid of EN1 expression, EN1+ progenitors and EN1 mRNA were abundant in cultures treated with FGF8b from day 9-16. FIG. 7E is a set of images showing the immunostaining of EN1, while FIG. 7G graphically represents mRNA levels of FOXA2, LMX1A, OTX2, and EN1 following qRT-PCR analysis.

In summation, treatment with FGF8b from day 9-16 further caused a significant decrease in the percentage of BARHL1+/FOXA2+ and PITX2+ STN progenitors, which is illustrated in FIGS. 7D-7F. This decrease indicated that late addition of FGF8b to cultures shifted progenitor fates from anterior ventral mesencephalon and STN fates toward caudal ventral mesencephalon mesDA progenitor fates.

Figure 7H:
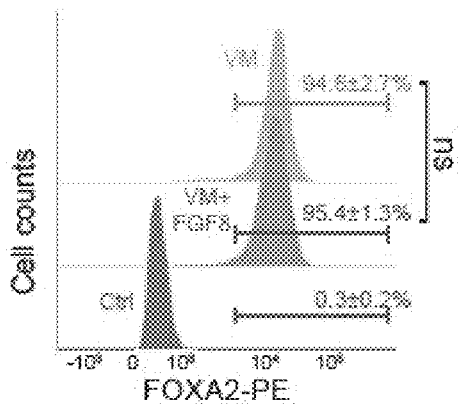
Figure 7I:
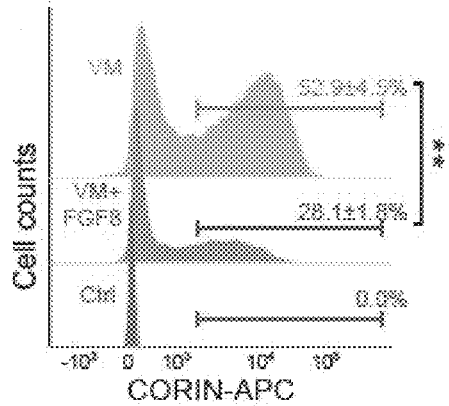

Flow cytometry analysis, exhibited as FACS plots in FIGS. 7H-7I, showed that although addition of FGF8b from day 9-16 did not affect the percentage of FOXA2 progenitors, there was a 47% decrease in the number of CORIN+ progenitors. This was in accordance with the negative correlations found for CORIN in the RNA sequencing analyses associated with FIGS. 5F-5G and indicates that CORIN expression both at the protein and mRNA level is more strongly associated with a rostral ventral mesencephalic/diencephalic fate rather than a caudal mesDA progenitor fate.

Example 9

To develop a GMP-compatible differentiation protocol for high and reproducible yield of caudilised mesDA ventral mesencephalon progenitors that would result in good graft outcome, a fully GMP-derived hES cell line RC17 from Roslin cells (hPS Creg #RCe021-A) was used. Previous research grade ventral mesencephalon differentiation protocols have implemented steps of embryoid body (EB) formation or culturing on MATRIGEL®, both of which pose problems in GMP adaptation due to difficulties in reproducibility and the content of undefined animal-derived component, respectively.

Figure 8A:
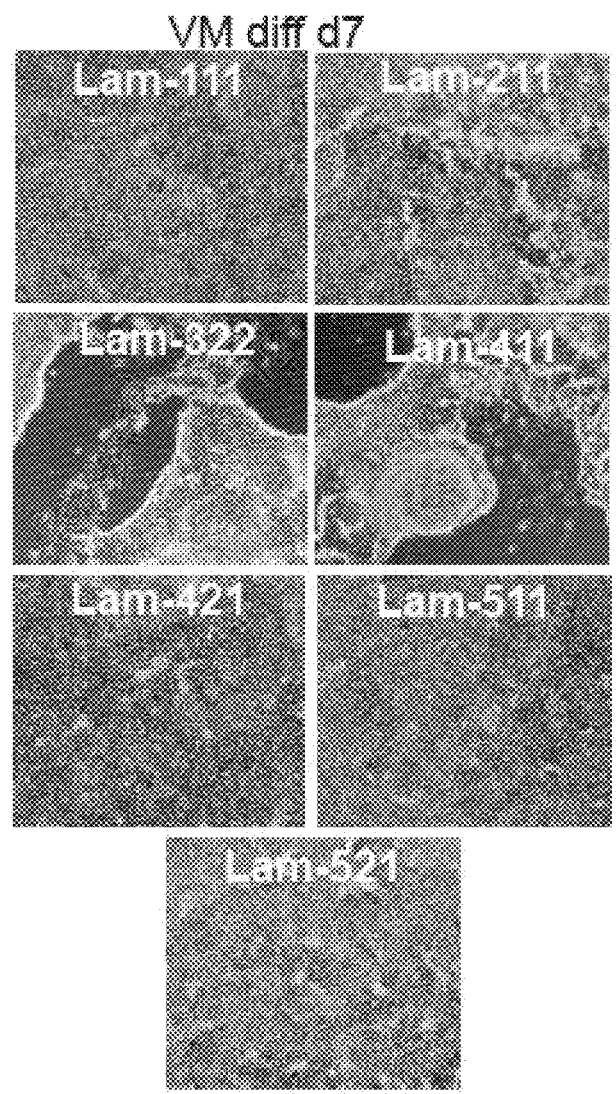
FIGS. 8A-8K are a set of images and graphs indicating that differentiation of hESCs on a GMP-compatible laminin-matrix produces high yield and purity of ventral mesencephalic progenitors. RC17 cells were used.

Seven different full-length laminin subtypes were tested, and it was found that four of them (LN-111, LN-421, LN-511, and LN-521) efficiently supported adherent differentiation of ventral mesencephalon progenitors from day 0-11 of the protocol. This is illustrated in FIG. 8A, which is a set of images revealing the best attachment and yield of neural cells across the seven tested laminin subtypes. Relative to a standard yield of 100%, LN-111 yielded 170%, LN-421 yielded 294%, LN-511 yielded 223%, and LN-521 yielded 208%. RC17 cells were differentiated according to the methods described herein, but on plates that were coated with laminin-121 instead of laminin-111. FIG. 8C compares the yields, and the yields are about equal to each other, i.e. LN-121 works about as well as LN-111 as a substrate.

Figure 8B:
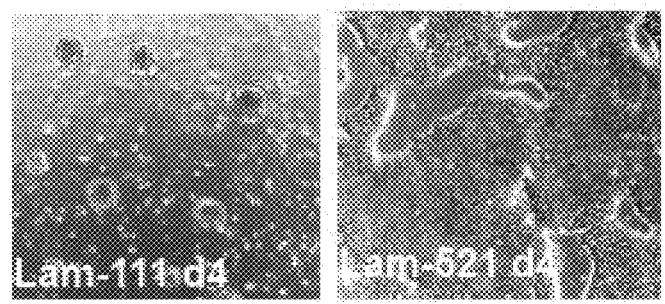
Figure 8C:
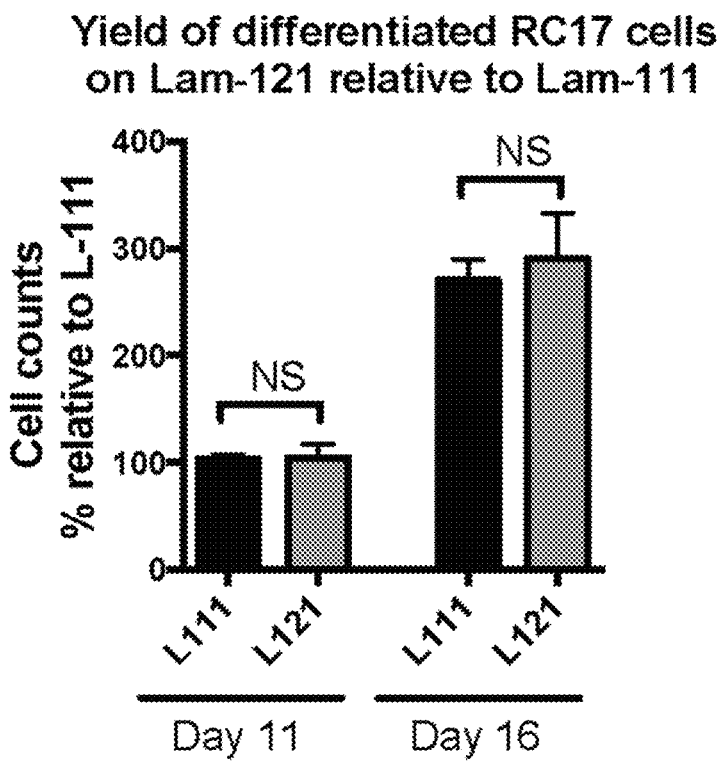
Figure 8D:
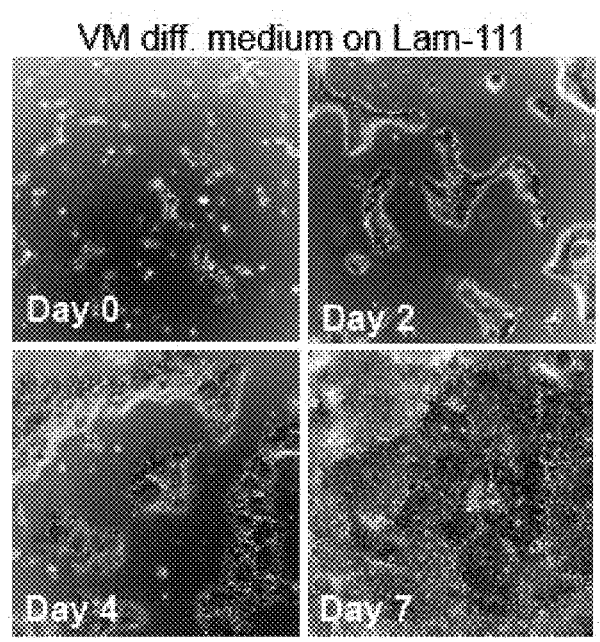
Figure 8E:
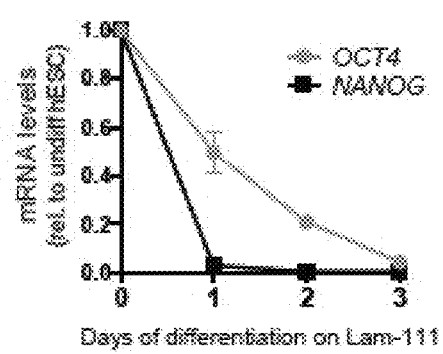

In contrast to LN-511 and LN-521, which efficiently support growth of hPSCs, it was found that when undifferentiated hESCs were plated onto LN-111 in pluripotency medium (iPS brew), the cells formed spheres after 4 days of culturing, that easily detached from the culture dish, as shown in the images of FIG. 8B. When the same number of cells was plated onto LN-111 in B27 medium, the cultures remained adherent and grew to confluency after 7 days of differentiation while showing rapid downregulation of pluripotency markers. FIG. 8D is a set of images taken at Days 0, 2, 4, and 7, exhibiting the seeding of low density hESCs on LN-111 matrix in B27 medium resulted in confluent neuralized cultures, while FIG. 8E is a graphical illustration of the pluripotency markers' mRNA levels decreasing over three days of differentiation. This indicated that LN-111 selectively supported the growth of neural cells but not pluripotent stem cells, which is in agreement with its broad expression in the developing brain.

Figure 8F:
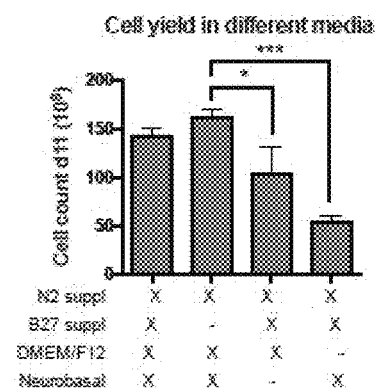

Next, different combinations of GMP-compatible basal medium was tested with the aim of optimizing the total yield and purity of ventral mesencephalon progenitors. It was found that the differentiation in a basal medium of NEUROBASAL® +DMEM/F12 with N2 supplement but without B27 supplement from day 0-11 produced the highest yield of cells on day 11. FIG. 8F is a graphical representation of the cell yield across the different media.

To ensure accurate caudalisation of the ventral mesencephalon progenitors, 100 ng/mL of FGF8b was added to the cells from day 9-16 of differentiation. For full GMP compatibility, all growth factors and chemicals in the protocol were switched to those enumerated in Table 4 below.

TABLE 4

| Reagent | Supplier | Cat. No. |
|---|---|---|
| For Differentiation | | |
| iPS brew | Miltenyi | 130-104-368 |
| LN-521 | BioLamina | LN-521 |
| LN-511 | BioLamina | LN-111 |
| DPBS + Ca + Mg (CTS) | LT | A12858-01 |
| EDTA | LT | 15575-020 |
| PBS -/- CTS | LT | A12856-01 |
| DMEM: F12 | LT | 21331-020 |
| NEUROBASAL ® CTS | LT | A13712-01 |
| N2 supplement CTS | LT | A13707-01 |
| B27 supplement w/o vitamin A | LT | 12587-010 |
| L Glutamine | LT | 25030-081 |
| AccutaseGMP | Innov. Cell Tech | AccutaseGMP |
| SB431542 | Miltenyi | 130-105-336 |
| CHIR99021 in 10 mM solution | Miltenyi | 130-106-539 |
| Y-27632 dihydrochloride | Miltenyi | 130-103-922 |
| Noggin GMP | R&D | 6057-GMP |
| BDNF GMP | R&D | 248-GMP |
| SHH C24II premium grade | Miltenyi | 130-095-727 |
| Ascorbic acid | Tocris | 4055 |
| FGF8b premium grade | Miltenyi | 130-095-740 |
| For Transplantation | | |
| HBSS (no Ca/Mg, no phenol red) | LT | 14175-046 |
| Pulmozyme (dornase alpha) | Roche | 11899 |

As illustrated in FIG. 2, the GMP-compatible protocol consisted of plating approximately $1 \times 10^6$ hESCs on a substrate containing LN-111, which were then cultured with N2 medium, SB431542, Noggin, Shh-C24II, and CHIR 99021 on days 0-9. The first culture was then removed and the plated cells were exposed to N2 medium and FGF8b on days 9-11, resulting in progenitors. The progenitor cells were then replated onto three separate plates at $0.8 \times 10^6/cm^2$ with a ROCK inhibitor (Y-27632). On days 11-16, the Y-27632 was removed and each plate was cultured in B27, FGF8b, BDNF, and ascorbic acid to result in cells covering an area of approximately $1.78 \pm 0.13 \times 10^6/cm^3$. This final yield was more than 40 times higher than the yield obtained with the original EB-based research grade differentiation protocol.

Figure 8G:
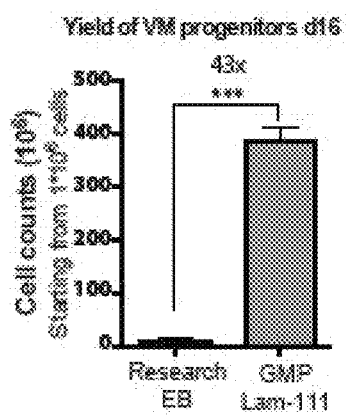

Based on these numbers, it was extrapolated that more than 380 million transplantable progenitor cells could be produced in 16 days when starting from 1 million undifferentiated hESCs. FIG. 8G is a graphical illustration of the counted cells from the EB-based protocol compared to the counted cells from the GMP/LN-111 protocol.

After terminally differentiating these progenitors in vitro, patch-clamp electrophysiology was performed on hESC differentiated to a ventral mesencephalon fate at day 45 post-differentiation. Cells grown on coverslips were submerged in a continuously flowing Krebs solution (119 mM NaCl, 2.5 mM KCl, 1.3 mM $MgSO_4$, 2.5 mM $CaCl_2$, 25 mM Glucose and 26 mM $NaHCO_3$) gassed with 95% $O_2$-5% $CO_2$ at 28° C. Recordings were made with a MULTI-CLAMP™ 700B amplifier (Molecular Devices), using borosilicate glass pipettes (3-7 MOhm) filled with 122.5 mM potassium gluconate, 12.5 mM KCl, 0.2 mM EGTA, 10 mM Hepes, 2 mM MgATP, 0.3 mM $Na_3GTP$ and 8 mM NaCl adjusted to pH 7.3 with KOH. Data was acquired with pCLAM™ 10.2 (Molecular Devices); current was filtered at 0.1 kHz and digitized at 2 kHz. Cells with neuronal morphology with round cell body were selected for whole-cell patch clamp. Resting membrane potentials were monitored immediately after breaking-in in current-clamp mode. Thereafter, cells were kept at a membrane potential of −60 mV to −80 mV, and 500 ms currents were injected from −20 pA to +90 pA with 10 pA increments to induce action potentials. For rebound depolarizations the cells were injected with a train of small currents of 20 pA to induce action potentials. Spontaneous post-synaptic currents were recorded at resting membrane potentials using the same internal solution.

Figure 8H:
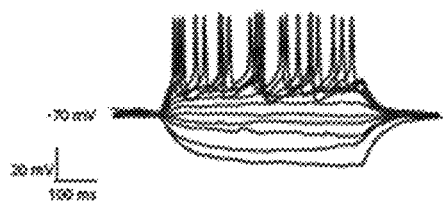
Figure 8I:
Figure 8J:
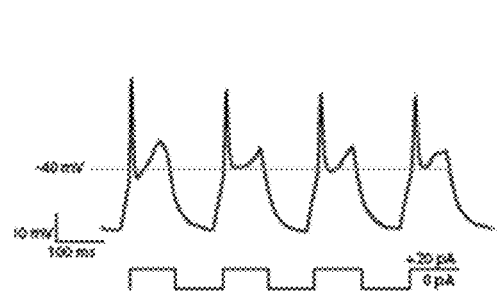
Figure 8K:
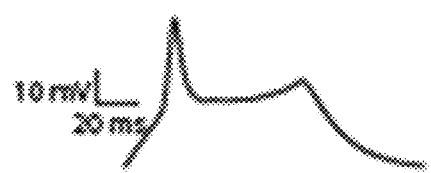

It was verified that the cells gave rise to neurons which evoked action potentials when assessed by patch clamp electrophysiology (11/11). In the mature fraction of neurons (resting membrane potential <−40 mV), 4 out of 7 cells further showed rebound action potentials after brief depolarization, which is characteristic of midbrain dopamine neurons in vitro. FIG. 8H is representative of the trace of action potentials induced with depolarizing current injections. FIG. 8I is a graph illustrating that some ventral mesencephalon cells showed spontaneous post-synaptic currents indicative of synaptic integration in the dish. FIG. 8J is an example of rebound depolarization after brief membrane depolarization characteristic of a dopaminergic phenotype. FIG. 8K is an inset from FIG. 8J showing a respective trace on an expanded scale.

Example 10

Figure 9A:
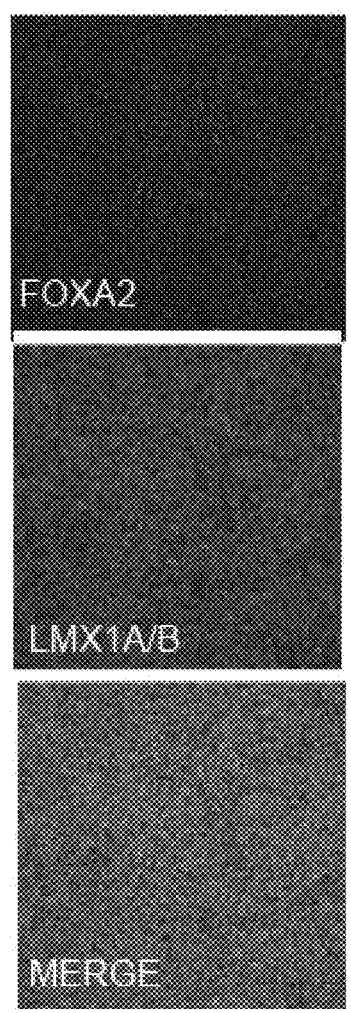
Figure 9B:
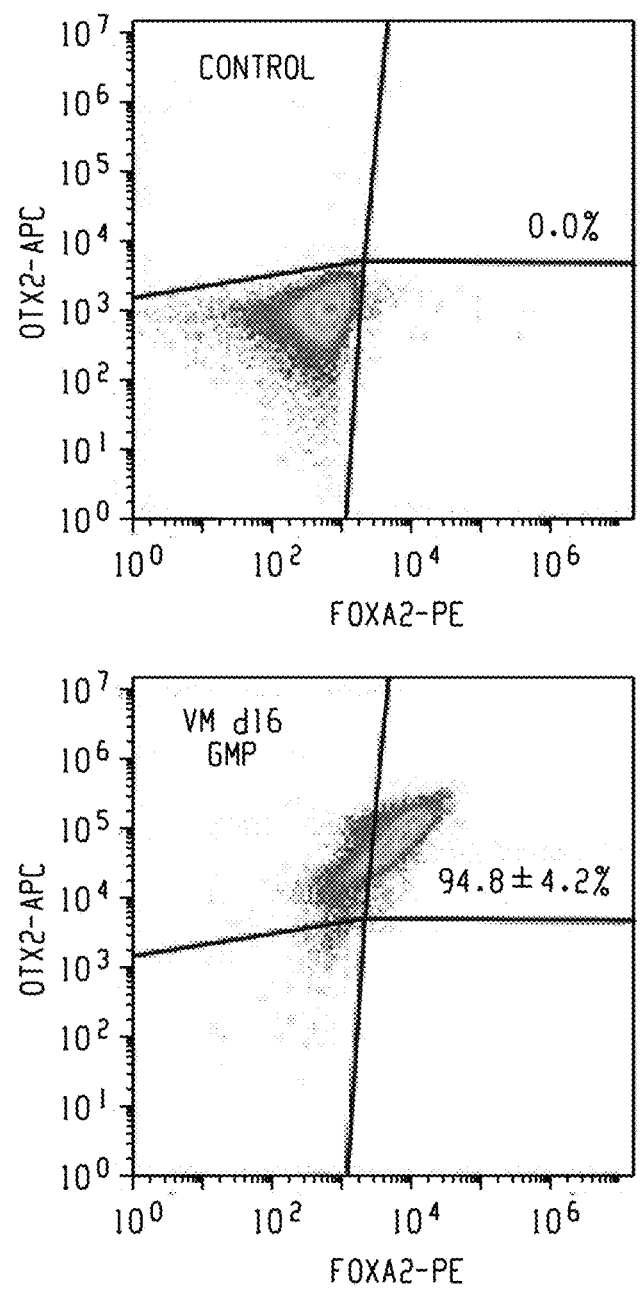

To validate that the new protocol of FIG. 3 gave rise to pure populations of ventral mesencephalon progenitors, cultures were stained for FOXA2 and LMX1A/B, and high co-localisation of the two proteins was found. FIG. 9A is a set of photographs after immunostaining the progenitors, illustrating that the cultures differentiated showed a very high overlap of LMX1A/FOXA2. FIG. 9B is a set of graphs following flow cytometry analysis, indicating the cultures contained on average 95% $OTX2^+/FOXA2^+$ progenitors on day 16 of differentiation.

To monitor batch-to-batch variations predictive of in vivo outcome, a qRT-PCR panel was designed implementing the new key predictive markers (EN1, SPRY1, PAX8, CNPY1, and ETV5). Human embryonic stem cells were differentiated according to the GMP protocol of Example 10, and then assessed on day 16 of differentiation for correct rostro-caudal ventral mesencephalon patterning as well as markers to monitor for the presence of any contaminating forebrain (FOXG1), hindbrain (HOXA2), or lateral (PAX6) cell populations. The specificities of all primers used in the panel were verified in samples of sub-dissected human fetal tissue enumerated in Table 5 below.

TABLE 5

| Gene | Full Gene Name | Primer Sequence (fwd/rev) |
|---|---|---|
| AADC | DDC (DOPA decarboxylase) | GGGGACCACAACATGCTGCTCC (SEQ ID NO: 1) AATGCACTGCCTGCGTAGGCTG (SEQ ID NO: 2) |
| ACTB | Beta-actin | CCTTGCACATGCCGGAG (SEQ ID NO: 3) GCACAGAGCCTCGCCTT (SEQ ID NO: 4) |
| BARHL1 | BarH-like homeobox 1 | GTACCAGAACCGCAGGACTAAA (SEQ ID NO: 5) AGAAATAAGGCGACGGGAACAT (SEQ ID NO: 6) |
| BARHL2 | BarH-like homeobox 2 | GGAGATTACGAGTAGCCGTGAG (SEQ ID NO: 7) AAGCTACGCTCCAGTTGATTGA (SEQ ID NO: 8) |
| CORIN | Corin, serin peptidase | CATATCTCCATCGCCTCAGTTG (SEQ ID NO: 9) GGCAGGAGTCCATGACTGT (SEQ ID NO: 10) |
| CNPY1 | Canopy FGF signaling regulator 1 | TTGGCCTCTCAAACACCATTCT (SEQ ID NO: 11) GAGCGAAACAAAACGCAATCAC (SEQ ID NO: 12) |
| EN1 | Engrailed 1 | CGTGGCTTACTCCCCATTTA (SEQ ID NO: 13) TCTCGCTGTCTCTCCCTCTC (SEQ ID NO: 14) |
| ETV5 | Ets Variant 5 | TCATCCTACATGAGAGGGGGTT (SEQ ID NO: 15) GACTTTGCCTTCCAGTCTCTCA (SEQ ID NO: 16) |
| FOXA2 | Forkhead box A2 | CCGTTCTCCATCAACAACCT (SEQ ID NO: 17) GGGGTAGTGCATCACCTGTT (SEQ ID NO: 18) |
| FOXG1 | Forkhead box G1 (BG1) | TGGCCCATGTCGCCCTTCCT (SEQ ID NO: 19) GCCGACGTGGTGCCGTTGTA (SEQ ID NO: 20) |
| FOXP2 | Forkhead box P2 | ATGAGCACTCTAAGCAGCCAAT (SEQ ID NO: 21) GTTGCAGATGCAGCAGTTCTAC (SEQ ID NO: 22) |
| GAPDH | Glyceraldehyde-3-phosphate dehydrogenase | TTGAGGTCAATGAAGGGGTC (SEQ ID NO: 23) GAAGGTGAAGGTCGGAGTCA (SEQ ID NO: 24) |
| GBX2 | Gastrulation brain homeobox 2 | GTTCCCGCCGTCGCTGATGAT (SEQ ID NO: 25) GCCGGTGTAGACGAAATGGCCG (SEQ ID NO: 26) |
| HOXA2 | Homeobox A2 | CGTCGCTCGCTGAGTGCCTG (SEQ ID NO: 27) TGTCGAGTGTGAAAGCGTCGAGG (SEQ ID NO: 28) |

TABLE 5 -continued

| Gene | Full Gene Name | Primer Sequence (fwd/rev) |
|---|---|---|
| LMX1A | Primers spanning 3' UTR of LMX1A | CGCATCGTTTCTTCTCCTCT (SEQ ID NO: 29)<br>CAGACAGACTTGGGGCTCAC (SEQ ID NO: 30) |
| LMX1B | LIM homeobox transcription factor b | CTTAACCAGCCTCAGCGACT (SEQ ID NO: 31)<br>TCAGGAGGCGAAGTAGGAAC (SEQ ID NO: 32) |
| NKX2.1 | NK2 homeobox 1 | AGGGCGGGGCACAGATTGGA (SEQ ID NO: 33)<br>GCTGGCAGAGTGTGCCCAGA (SEQ ID NO: 34) |
| NURR1 | NR4a2 | CAGGCGTTTTCGAGGAAAT (SEQ ID NO: 35)<br>GAGACGCGGAGAACTCCTAA (SEQ ID NO: 36) |
| OCT4 | POU5F1 | TCTCCAGGTTGCCTCTCACT (SEQ ID NO: 37)<br>GTGGAGGAAGCTGACAACAA (SEQ ID NO: 38) |
| OTX2 | Orthodenticle homeobox 2 | ACAAGTGGCCAATTCACTCC (SEQ ID NO: 39)<br>GAGGTGGACAAGGGATCTGA (SEQ ID NO: 40) |
| PAX8 | Paired box 8 | ATAGCTGCCGACTAAGCATTGA (SEQ ID NO: 41)<br>ATCCGTGCGAAGGTGCTTT (SEQ ID NO: 42) |
| PITX3 | Paired-like homeodomain 3 | GGAGGTGTACCCCGGCTACTCG (SEQ ID NO: 43)<br>GAAGCCAGAGGCCCCACGTTGA (SEQ ID NO: 44) |
| SHH | Sonic hedgehog | CCAATTACAACCCCGACATC (SEQ ID NO: 45)<br>AGTTTCACTCCTGGCCACTG (SEQ ID NO: 46) |
| SIM1 | Single-minded homolog 1 | AAAGGGGGCCAAATCCCGGC (SEQ ID NO: 47)<br>TCCGCCCCACTGGCTGTCAT (SEQ ID NO: 48) |
| SIX3 | SIX homeobox 3 | ACCGGCCTCACTCCCACACA (SEQ ID NO: 49)<br>CGCTCGGTCCAATGGCCTGG (SEQ ID NO: 50) |
| SOX1 | SRY (sex determining region Y)-box 1 | GGGAAAACGGGCAAAATAAT (SEQ ID NO: 51)<br>TTTTGCGTTCACATCGGTTA (SEQ ID NO: 52) |
| SPRY1 | Sprouty 1 | GCCCTGGATAAGGAACAGCTAC (SEQ ID NO: 53)<br>GCCGAAATGCCTAATGCAAAGA (SEQ ID NO: 54) |
| TH | Tyrosine hydroxylase | CGGGCTTCTCGGACCAGGTGTA (SEQ ID NO: 55)<br>CTCCTCGGCGGTGTACTCCACA (SEQ ID NO: 56) |
| WNT1 | Wingless-type MMTV integration site family, member 1 | GAGCCACGAGTTTGGATGTT (SEQ ID NO: 57)<br>TGCAGGGAGAAAGGAGAGAA (SEQ ID NO: 58) |

To assess the reproducibility and accuracy of the new GMP protocol compared to the research-grade protocol, 34 research grade and 43 GMP ventral mesencephalic batches were analyzed using the designed qRT-PCR panel.

FIG. 9C is an image of comparing hESCs differentiated according to the two protocols. The hESCs were assessed for RNA expression on day 16 of differentiation. Differentiations toward ventral forebrain (vFB) and ventral hindbrain (vHB) were included as controls. Values were color-coded and normalized to the sample with the highest gene expression for each gene.

While all batches of cells had very robust expression of OTX1, OTX2, LMX1A, LMX1B, and FOXA2, there was considerable variation in the expression of caudal ventral mesencephalon markers PAX8, EN1, SPRY1, and ETV5 between batches generated with the research-grade protocol. The research grade cell batches generally tended to fall into two categories: (i) cell batches with high levels of EN1, PAX8, ETV5, SPRY1, and HOXA2; or (ii) cell batches with low levels of EN1, PAX8, ETV5, SPRY1, and HOXA2, while only very few batches contained high levels of caudal ventral mesencephalon markers (EN1, PAX8, ETV5, SPRY1) in the absence of HOXA2 expression.

These expression patterns indicated that the presence of hindbrain cells (HOXA2$^+$) was necessary for induction of a full caudal ventral mesencephalic identity in the cultures generated by the research grade protocol, since the absence of hindbrain cells yielded cultures with a predominantly rostral ventral mesencephalic identity. In contrast, implementation of the new GMP protocol yielded batches of cells which were more homogenous and which did not contain high levels of HOXA2 contamination.

Addition of FGF8b to the GMP protocol (day 9-16) caused robustly induced high-level expression of caudal ventral mesencephalon markers (EN1, PAX8, ETV5, and SPRY1), which had been shown to be predictive of DA yield concomitantly with a reduction in the expression of markers negatively correlated with high DA yield (CORIN and FOXP2). This caudalisation took place in the absence of HOXA2 contamination. When assessing grafts from two clinically relevant cell lines (H9 and RC17) differentiated according to the GMP protocol of Example 10, it was found that both lines generated neuron rich grafts with a high number of TH-expressing cells. FIG. 9D (H9) and FIG. 9E (RC17) are representative images of grafts from batches containing high levels of caudal ventral mesencephalon markers. These cells densely innervated the host striatum (see those labeled with D" and E") and expressed mature mesDA markers. The protocol had decreased hindbrain contamination and increased expression of caudal ventral mesencephalon markers, which were predictive of a good graft outcome.

Example 11

To determine if the GMP protocol yielded cells with functional dopaminergic activity in vivo and if the anterior versus caudal VM phenotypes were truly predictive of in vivo efficacy, the cells were assessed by transplantation to an animal model of Parkinson's Disease. Two groups of rats subjected to unilateral 6-OHDA lesions were assessed for amphetamine-induced rotations before and after intrastriatal transplantation with VM-patterned RC17 cells differentiated according to the LN-111 GMP protocol (protocol in FIG. 2). One group of animals (mesDA RC17) received cells differentiated in the presence of FGF8b from day 9-16 to yield caudal VM mesDA progenitors expressing high levels of predictive markers EN1, CNPY1, SPRY1, ETV5 and PAX8 as shown in FIG. 9C. As exhibited in FIG. 10, this group of animals exhibited functional recovery as evidenced by reversal and overcompensation (by week 22) of amphetamine-induced rotations. A decrease in rotations is equivalent to behavioral recovery, as the lesions cause rotation in the rats. If the graft is functional, the rotational behavior is abolished. In contrast, animals receiving cells differentiated in the absence of FGF8b to yield rostral VM cells of the STN domain (STN RC17 group) did not exhibit functional recovery of amphetamine-induced rotations. These STN-patterned cells expressed high levels of general VM markers but low levels of predictive caudal VM markers, thereby validating the power of the caudal VM markers for predicting in vivo outcome in animal models of Parkinson's Disease.

DISCUSSION

Pre-clinical evaluation of cells and their in vivo performance is pertinent because for disorders of the central nervous system, transplantation is performed with immature progenitor cells that undergo terminal differentiation and maturation after transplantation in vivo. Transplanted progenitors only become functional after several months in vivo. This complicates the assessment of the therapeutic potential of the cells prior to grafting. It is thus desirable to be able to predict the in vivo maturation of grafted cells based on in vitro characteristics of the progenitors prior to grafting.

It was found that in vitro differentiation into TH+ neurons does not correlate with the formation of TH+ neurons in vivo. It was also found that although FOXA2, LMX1A and CORIN, which are commonly used to identify mesDA progenitors during development and in stem cell cultures, are necessary for dopamine differentiation after transplantation, they are not sufficient to predict yield or functionality of the cells in vivo. This highlights the need to validate markers that can predict functional maturation of the cell in vivo, rather than relying solely on markers expressed in the differentiating progenitors of a specific cell lineage.

When applying an unbiased approach to identifying predictive markers of successful graft outcome, it was found that markers expressed by midbrain cells close to the MHB (i.e. EN1, ETV5, CNPY1, PAX8 and SPRY1) correlated with a successful graft outcome, while markers expressed in the diencephalic domain, such as EPHA3, showed a negative correlation with graft outcome. These findings are in line with a recent study in the mouse model showing a remarkably close relationship between mesDA and STN neuronal lineages. Whereas many key transcription factors, including LMX1A, LMX1B, CORIN, FOXA1, FOXA2, FOXP1, FOXP2, MSX1, NURR1, and PBX1, are shared by both lineages, only the mesDA lineage is identified by expression of EN1 and CNPY1, which are restricted to the caudal part of the ventral mesencephalon.

Based on analyzing these markers, it was confirmed that the ventral mesencephalic-patterned cultures contained both STN and mesDA progenitors and that their relative proportion in each batch likely contributed to the observed, but previously unexplained, variation in in vivo outcome when progenitors defined only by high co-expression of LMX1A, FOXA2 and OTX2 were transplanted.

Fine tuning the patterning to enrich for dopaminergic progenitors was achieved via timed, exogenous delivery of FGF8b at the progenitor stage of differentiation. This, as well as a number of adjustments, allowed the generation of a full GMP differentiation protocol for the production of mesDA progenitors. Key to this GMP protocol is the use of LN-111, a physiologically relevant extracellular matrix component that is normally expressed in the developing brain and which was found to support attachment of differentiating neural progenitors but not pluripotent stem cells.

From post-mortem brain analysis of Parkinson's Disease patients transplanted with human fetal ventral mesencephalic tissue, it was determined that grafts containing approximately 100,000 transplanted TH+ neurons are associated with significant clinical benefit in patients. Using the laminin-based GMP protocol, the number of mesDA progenitors obtained per hESC at start of differentiation was greatly increased compared to the research grade protocol, and resulted in graft outcomes matching the best differentiations from the research grade protocol. Given an average yield of about 5000 to 6000 mature DA neurons per 100,000 transplanted progenitors from cell batches high in the predictive markers, manual production of cells for several hundred patients can be achievable even in small GMP labs without the need for automated culture systems. The protocol presented here omits many of the large-scale production issues associated with other stem cell therapies going into a clinic.

Figure 10:
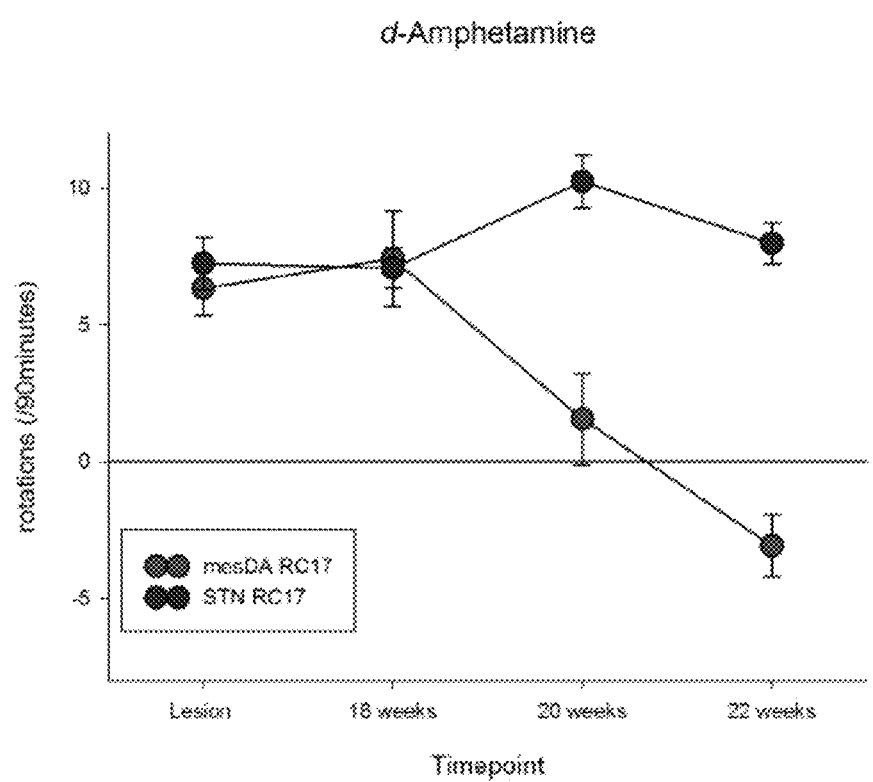
FIG. 10 is a graphical representation of behavioral recovery in an animal model of Parkinson's Disease. Rats subjected to unilateral 6-OHDA lesions were assessed for amphetamine-induced rotations before and after transplantation with RC17 cells differentiated according to the LN-111 GMP protocol. One group of animals (mesDA RC17, green dots) was transplanted with cells differentiated in the presence of FGF8b from day 9-16 to yield caudalised VM cells of the mesencephalic dopamine (mesDA) domain. This group exhibited functional recovery as evidenced by reversal and overcompensation (by week 22) of amphetamine-induced rotations. The other group (STN RC17, red dots) was transplanted with cells differentiated in the absence of FGF8b to yield rostral VM cells of the STN domain. In contrast to the mesDA group, the STN group did not exhibit functional recovery of amphetamine-induced rotations.

Further, the in vivo efficacy of the GMP protocol as well as the predictive powers of the newly identified markers listed above were verified in Example 11 and FIG. 10. A decrease in rotations was considered equivalent to behavioral recovery, as the dopaminergic 6-OHDA lesions caused animals to rotate. A graft was considered functional if it abolished the rotational behavior down to or below the baseline of 0.

The global gene profiling of a large number of cell batches that have been transplanted into a rat model allowed the establishment of a panel of markers to much more precisely predict a successful graft outcome at the progenitor stage in vitro. The ability to better predict graft outcome will accelerate the progression of stem cells towards clinical use and can be used for batch-to-batch comparability as well as to compare the cells grafted in different clinical trials. In the long term, a better prediction of in vivo maturation and functional properties of the cells already at the progenitor level will facilitate the use of autologous or individually matched cells for transplantation.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A method for inducing production of dopaminergic cells, comprising:
   (a) plating pluripotent stem cells on a substrate coated with laminin-111, laminin-121, laminin-521, laminin-421, or laminin-511,
   (b) culturing the plated cells in a first medium comprising a neural induction medium or an N2 medium; a rho-associated kinase (ROCK) inhibitor; a transforming growth factor beta (TGF-β) inhibitor; and a glycogen synthase kinase 3 (GSK3) inhibitor,
   (c) removing the first medium and adding a second medium comprising a neural induction medium or an N2 medium; a TGF-β inhibitor, and a GSK3 inhibitor, and not containing a ROCK inhibitor,
   (d) removing the second medium and adding a third medium comprising (i) a neural proliferation medium or an N2 medium; and (ii) a TGF-β inhibitor, and optionally also contains sonic hedgehog protein,
   (e) replacing the third medium with a fourth medium comprising (i) a neural proliferation medium (NPM) or an N2 medium; and (ii) a fibroblast growth factor (FGF),
   (f) replating the cells on a second plate coated with laminin-111, laminin-121, laminin-521, laminin-421, or laminin-511, and
   (g) culturing the replated cells in a fifth medium comprising a B27 medium; a brain derived neurotrophic factor (BDNF); ascorbic acid (AA); a glial cell line-derived neurotrophic factor (GDNF); and a fibroblast growth factor (FGF).

2. The method of claim 1, wherein the cells are passaged with ethylenediaminetetraacetic acid (EDTA) prior to the plating.

3. The method of claim 1, wherein the FGF is FGF8b.

4. The method of claim 1, wherein the second medium is added about 36 hours to about 60 hours after the plating.

5. The method of claim 1, wherein the second medium further contains about 0.2 µM or more of the GSK3 inhibitor and about 50 ng/mL or more of the sonic hedgehog protein;
   wherein the second medium contains about 0.2 µM to about 0.4 µM of the GSK3 inhibitor for diencephalic fates;
   wherein the second medium contains about 0.6 µM to about 0.8 µM of the GSK3 inhibitor for mesencephalic fates;
   wherein the second medium contains about 1 µM to about 2 µM of the GSK3 inhibitor for anterior rhomencephalic fates;
   wherein the second medium contains at least 4 µM of the GSK3 inhibitor for posterior rhomencephalic fates;
   wherein the first medium and the second medium comprise about 50 ng/mL to about 150 ng/mL of the sonic hedgehog protein for basal plate fates;
   wherein the first medium and the second medium contains at least 200 ng/mL of the sonic hedgehog protein for floor plate fates; or
   wherein bone morphogenic protein inhibitors are not present in the second medium after day 4 for roof plate fates.

6. The method of claim 1, wherein the third medium is added about 84 hours to about 108 hours after the plating.

7. The method of claim 6, wherein the third medium is also renewed about 156 hours to about 180 hours after the plating of (a).

8. The method of claim 1, wherein the fourth medium is added about 156 hours to about 228 hours after the plating.

9. The method of claim 8, wherein the FGF is FGF8b.

10. The method of claim 1, wherein the cells are replated about 252 hours to about 276 hours after the plating of (a).

11. The method of claim 1, further comprising renewing the fifth medium about 324 hours to about 348 hours after the plating of (a).

12. The method of claim 1, wherein after production, the dopaminergic cells are maintained on laminin-111, laminin-121, laminin-521, laminin-421, or laminin-511 until transplantation or cryopreservation.

\* \* \* \* \*

SEQUENCE LISTING

```
<160> NUMBER OF SEQ ID NOS: 58

<210> SEQ ID NO 1
<211> LENGTH: 22
<212> TYPE: DNA
<213> ORGANISM: Homo sapiens

<400> SEQUENCE: 1
ggggaccaca acatgctgct cc                                                  22

<210> SEQ ID NO 2
<211> LENGTH: 22
<212> TYPE: DNA
<213> ORGANISM: Homo sapiens

<400> SEQUENCE: 2
aatgcactgc ctgcgtaggc tg                                                  22

<210> SEQ ID NO 3
<211> LENGTH: 17
<212> TYPE: DNA
<213> ORGANISM: Homo sapiens

<400> SEQUENCE: 3
ccttgcacat gccggag                                                        17

<210> SEQ ID NO 4
<211> LENGTH: 17
<212> TYPE: DNA
<213> ORGANISM: Homo sapiens

<400> SEQUENCE: 4
gcacagagcc tcgcctt                                                        17

<210> SEQ ID NO 5
<211> LENGTH: 22
<212> TYPE: DNA
<213> ORGANISM: Homo sapiens
```

<400> SEQUENCE: 5
gtaccagaac cgcaggacta aa                                          22

<210> SEQ ID NO 6
<211> LENGTH: 22
<212> TYPE: DNA
<213> ORGANISM: Homo sapiens

<400> SEQUENCE: 6
agaaataagg cgacgggaac at                                          22

<210> SEQ ID NO 7
<211> LENGTH: 22
<212> TYPE: DNA
<213> ORGANISM: Homo sapiens

<400> SEQUENCE: 7
ggagattacg agtagccgtg ag                                          22

<210> SEQ ID NO 8
<211> LENGTH: 22
<212> TYPE: DNA
<213> ORGANISM: Homo sapiens

<400> SEQUENCE: 8
aagctacgct ccagttgatt ga                                          22

<210> SEQ ID NO 9
<211> LENGTH: 22
<212> TYPE: DNA
<213> ORGANISM: Homo sapiens

<400> SEQUENCE: 9
catatctcca tcgcctcagt tg                                          22

<210> SEQ ID NO 10
<211> LENGTH: 19
<212> TYPE: DNA
<213> ORGANISM: Homo sapiens

<400> SEQUENCE: 10
ggcaggagtc catgactgt                                              19

<210> SEQ ID NO 11
<211> LENGTH: 22
<212> TYPE: DNA
<213> ORGANISM: Homo sapiens

<400> SEQUENCE: 11
ttggcctctc aaacaccatt ct                                          22

<210> SEQ ID NO 12
<211> LENGTH: 22
<212> TYPE: DNA
<213> ORGANISM: Homo sapiens

<400> SEQUENCE: 12
gagcgaaaca aaacgcaatc ac                                          22

<210> SEQ ID NO 13
<211> LENGTH: 20
<212> TYPE: DNA
<213> ORGANISM: Homo sapiens

```
<400> SEQUENCE: 13
cgtggcttac tccccattta                                                    20

<210> SEQ ID NO 14
<211> LENGTH: 20
<212> TYPE: DNA
<213> ORGANISM: Homo sapiens

<400> SEQUENCE: 14
tctcgctgtc tctccctctc                                                    20

<210> SEQ ID NO 15
<211> LENGTH: 22
<212> TYPE: DNA
<213> ORGANISM: Homo sapiens

<400> SEQUENCE: 15
tcatcctaca tgagaggggg tt                                                 22

<210> SEQ ID NO 16
<211> LENGTH: 22
<212> TYPE: DNA
<213> ORGANISM: Homo sapiens

<400> SEQUENCE: 16
gactttgcct tccagtctct ca                                                 22

<210> SEQ ID NO 17
<211> LENGTH: 20
<212> TYPE: DNA
<213> ORGANISM: Homo sapiens

<400> SEQUENCE: 17
ccgttctcca tcaacaacct                                                    20

<210> SEQ ID NO 18
<211> LENGTH: 20
<212> TYPE: DNA
<213> ORGANISM: Homo sapiens

<400> SEQUENCE: 18
ggggtagtgc atcacctgtt                                                    20

<210> SEQ ID NO 19
<211> LENGTH: 20
<212> TYPE: DNA
<213> ORGANISM: Homo sapiens

<400> SEQUENCE: 19
tggcccatgt cgcccttcct                                                    20

<210> SEQ ID NO 20
<211> LENGTH: 20
<212> TYPE: DNA
<213> ORGANISM: Homo sapiens

<400> SEQUENCE: 20
gccgacgtgg tgccgttgta                                                    20

<210> SEQ ID NO 21
<211> LENGTH: 22
<212> TYPE: DNA
```

```
<213> ORGANISM: Homo sapiens

<400> SEQUENCE: 21
atgagcactc taagcagcca at                                              22

<210> SEQ ID NO 22
<211> LENGTH: 22
<212> TYPE: DNA
<213> ORGANISM: Homo sapiens

<400> SEQUENCE: 22
gttgcagatg cagcagttct ac                                              22

<210> SEQ ID NO 23
<211> LENGTH: 20
<212> TYPE: DNA
<213> ORGANISM: Homo sapiens

<400> SEQUENCE: 23
ttgaggtcaa tgaaggggtc                                                 20

<210> SEQ ID NO 24
<211> LENGTH: 20
<212> TYPE: DNA
<213> ORGANISM: Homo sapiens

<400> SEQUENCE: 24
gaaggtgaag gtcggagtca                                                 20

<210> SEQ ID NO 25
<211> LENGTH: 21
<212> TYPE: DNA
<213> ORGANISM: Homo sapiens

<400> SEQUENCE: 25
gttcccgccg tcgctgatga t                                               21

<210> SEQ ID NO 26
<211> LENGTH: 22
<212> TYPE: DNA
<213> ORGANISM: Homo sapiens

<400> SEQUENCE: 26
gccggtgtag acgaaatggc cg                                              22

<210> SEQ ID NO 27
<211> LENGTH: 20
<212> TYPE: DNA
<213> ORGANISM: Homo sapiens

<400> SEQUENCE: 27
cgtcgctcgc tgagtgcctg                                                 20

<210> SEQ ID NO 28
<211> LENGTH: 23
<212> TYPE: DNA
<213> ORGANISM: Homo sapiens

<400> SEQUENCE: 28
tgtcgagtgt gaaagcgtcg agg                                             23

<210> SEQ ID NO 29
<211> LENGTH: 20
```

```
<212> TYPE: DNA
<213> ORGANISM: Homo sapiens

<400> SEQUENCE: 29
cgcatcgttt cttctcctct                                          20

<210> SEQ ID NO 30
<211> LENGTH: 20
<212> TYPE: DNA
<213> ORGANISM: Homo sapiens

<400> SEQUENCE: 30
cagacagact tggggctcac                                          20

<210> SEQ ID NO 31
<211> LENGTH: 20
<212> TYPE: DNA
<213> ORGANISM: Homo sapiens

<400> SEQUENCE: 31
cttaaccagc ctcagcgact                                          20

<210> SEQ ID NO 32
<211> LENGTH: 20
<212> TYPE: DNA
<213> ORGANISM: Homo sapiens

<400> SEQUENCE: 32
tcaggaggcg aagtaggaac                                          20

<210> SEQ ID NO 33
<211> LENGTH: 20
<212> TYPE: DNA
<213> ORGANISM: Homo sapiens

<400> SEQUENCE: 33
agggcggggc acagattgga                                          20

<210> SEQ ID NO 34
<211> LENGTH: 20
<212> TYPE: DNA
<213> ORGANISM: Homo sapiens

<400> SEQUENCE: 34
gctggcagag tgtgcccaga                                          20

<210> SEQ ID NO 35
<211> LENGTH: 19
<212> TYPE: DNA
<213> ORGANISM: Homo sapiens

<400> SEQUENCE: 35
caggcgtttt cgaggaaat                                           19

<210> SEQ ID NO 36
<211> LENGTH: 20
<212> TYPE: DNA
<213> ORGANISM: Homo sapiens

<400> SEQUENCE: 36
gagacgcgga gaactcctaa                                          20

<210> SEQ ID NO 37
```

```
<211> LENGTH: 20
<212> TYPE: DNA
<213> ORGANISM: Homo sapiens

<400> SEQUENCE: 37
tctccaggtt gcctctcact                                              20

<210> SEQ ID NO 38
<211> LENGTH: 20
<212> TYPE: DNA
<213> ORGANISM: Homo sapiens

<400> SEQUENCE: 38
gtggaggaag ctgacaacaa                                              20

<210> SEQ ID NO 39
<211> LENGTH: 20
<212> TYPE: DNA
<213> ORGANISM: Homo sapiens

<400> SEQUENCE: 39
acaagtggcc aattcactcc                                              20

<210> SEQ ID NO 40
<211> LENGTH: 20
<212> TYPE: DNA
<213> ORGANISM: Homo sapiens

<400> SEQUENCE: 40
gaggtggaca agggatctga                                              20

<210> SEQ ID NO 41
<211> LENGTH: 22
<212> TYPE: DNA
<213> ORGANISM: Homo sapiens

<400> SEQUENCE: 41
atagctgccg actaagcatt ga                                           22

<210> SEQ ID NO 42
<211> LENGTH: 19
<212> TYPE: DNA
<213> ORGANISM: Homo sapiens

<400> SEQUENCE: 42
atccgtgcga aggtgctتt                                               19

<210> SEQ ID NO 43
<211> LENGTH: 22
<212> TYPE: DNA
<213> ORGANISM: Homo sapiens

<400> SEQUENCE: 43
ggaggtgtac cccggctact cg                                           22

<210> SEQ ID NO 44
<211> LENGTH: 22
<212> TYPE: DNA
<213> ORGANISM: Homo sapiens

<400> SEQUENCE: 44
gaagccagag gccccacgtt ga                                           22
```

```
<210> SEQ ID NO 45
<211> LENGTH: 20
<212> TYPE: DNA
<213> ORGANISM: Homo sapiens

<400> SEQUENCE: 45
ccaattacaa ccccgacatc                                                   20

<210> SEQ ID NO 46
<211> LENGTH: 20
<212> TYPE: DNA
<213> ORGANISM: Homo sapiens

<400> SEQUENCE: 46
agtttcactc ctggccactg                                                   20

<210> SEQ ID NO 47
<211> LENGTH: 20
<212> TYPE: DNA
<213> ORGANISM: Homo sapiens

<400> SEQUENCE: 47 aaaggggggcc aaatcccggc                                                  20

<210> SEQ ID NO 48
<211> LENGTH: 20
<212> TYPE: DNA
<213> ORGANISM: Homo sapiens

<400> SEQUENCE: 48
tccgccccac tggctgtcat                                                   20

<210> SEQ ID NO 49
<211> LENGTH: 20
<212> TYPE: DNA
<213> ORGANISM: Homo sapiens

<400> SEQUENCE: 49
accggcctca ctcccacaca                                                   20

<210> SEQ ID NO 50
<211> LENGTH: 20
<212> TYPE: DNA
<213> ORGANISM: Homo sapiens

<400> SEQUENCE: 50
cgctcggtcc aatggcctgg                                                   20

<210> SEQ ID NO 51
<211> LENGTH: 20
<212> TYPE: DNA
<213> ORGANISM: Homo sapiens

<400> SEQUENCE: 51
gggaaaacgg gcaaaataat                                                   20

<210> SEQ ID NO 52
<211> LENGTH: 20
<212> TYPE: DNA
<213> ORGANISM: Homo sapiens

<400> SEQUENCE: 52
ttttgcgttc acatcggtta                                                   20
```

```
<210> SEQ ID NO 53
<211> LENGTH: 22
<212> TYPE: DNA
<213> ORGANISM: Homo sapiens

<400> SEQUENCE: 53
gccctggata aggaacagct ac                                                  22

<210> SEQ ID NO 54
<211> LENGTH: 22
<212> TYPE: DNA
<213> ORGANISM: Homo sapiens

<400> SEQUENCE: 54
gccgaaatgc ctaatgcaaa ga                                                  22

<210> SEQ ID NO 55
<211> LENGTH: 22
<212> TYPE: DNA
<213> ORGANISM: Homo sapiens

<400> SEQUENCE: 55
cgggcttctc ggaccaggtg ta                                                  22

<210> SEQ ID NO 56
<211> LENGTH: 22
<212> TYPE: DNA
<213> ORGANISM: Homo sapiens

<400> SEQUENCE: 56
ctcctcggcg gtgtactcca ca                                                  22

<210> SEQ ID NO 57
<211> LENGTH: 20
<212> TYPE: DNA
<213> ORGANISM: Homo sapiens

<400> SEQUENCE: 57
gagccacgag tttggatgtt                                                     20

<210> SEQ ID NO 58
<211> LENGTH: 20
<212> TYPE: DNA
<213> ORGANISM: Homo sapiens

<400> SEQUENCE: 58
tgcagggaga aaggagagaa                                                     20
```